United States Patent [19]
Shimono et al.

[11] Patent Number: 5,748,305
[45] Date of Patent: May 5, 1998

[54] METHOD AND APPARATUS FOR PARTICLE INSPECTION

[75] Inventors: Ken Shimono; Tatsuo Nagasaki, both of Hirakata; Kenji Takamoto, Neyagawa; Masami Ito, Moriguchi; Kanji Nishii, Osaka, all of Japan

[73] Assignee: Matsushita Electric Industrial Co., Ltd., Osaka-fu, Japan

[21] Appl. No.: 670,851

[22] Filed: Jun. 28, 1996

[30] Foreign Application Priority Data

Jun. 30, 1995 [JP] Japan .................................. 7-166208

[51] Int. Cl.$^6$ ........................................ G01N 21/00
[52] U.S. Cl. .......................... 356/237; 356/338; 356/340; 356/343; 250/572
[58] Field of Search ........................ 356/237, 335, 356/338, 343, 340, 339; 250/572

[56] References Cited

U.S. PATENT DOCUMENTS

| | | | |
|---|---|---|---|
| 5,331,396 | 7/1994 | Yukawa et al. | 356/237 |
| 5,363,187 | 11/1994 | Hagiwara et al. | 356/237 |

OTHER PUBLICATIONS

Keisoku-jidoseigyo-gakkai, vol. 17, No. 2, pp. 237–242, issued Apr. 1981 by N. Akiyama et al. (Hitachi), entitled "Automtic Inspection of Foreign Particles on Patterned Sample by Means of Polarized Laser".

Keisoku-jidoseigyo-gakki, vol. 25, No. 9, pp. 954–961, issued 1989 by M. Koizumi et al. (Hitachi), entitled "Contaiminant Detection Method Utilizing Polarization Characteristics of Light Reflected from LSI Patterns".

*Primary Examiner*—David C. Nelms
*Assistant Examiner*—Reginald A. Ratliff
*Attorney, Agent, or Firm*—Wenderoth, Lind & Ponack

[57] ABSTRACT

A method for foreign particles inspection includes illuminating an inspection surface of an inspection object with a beam which is, one of s-polarized and p-polarized relative to the inspection surface of the inspection object. The illumination utilizes an optical axis which is generally parallel to the inspection surface or which intersects the inspection surface at an angle that is greater than or equal to 1° and less than 5°. Reflected and scattered light is detected utilizing an optical axis which makes an acute angle with the inspection surface and which makes a differential angle of 30° or less with the optical axis of the illumination beam. The detection of foreign particles is accomplished by detecting the component of the reflected and scattered light which is the other of s-polarized and p-polarized relative to the inspection surface.

36 Claims, 14 Drawing Sheets

RELATIVE RATIO TO S/N VALUE ON OPTICAL AXIS

IMAGE HEIGHT (CENTER OF FIELD OF VIEW)   (END OF FIELD OF VIEW)

5,748,305

METHOD AND APPARATUS FOR PARTICLE INSPECTION

BACKGROUND OF THE INVENTION

The present invention relates to a method and an apparatus for inspecting defects other than a pattern, i.e., contaminant or foreign particles such as chips, dust, flaws, or human dandruff present on the surface of an inspection object. More particularly, the present invention relates to a method and an apparatus for use in carrying out an external appearance inspection of patterned substrates in manufacturing stages, such as liquid crystal fabrication and semiconductor fabrication.

A conventional method for foreign particles inspection is described in, for example, a Japanese academic publication, "Keisoku Jido Seigyo Gakkai Ronbunshu," Vol., 17, No. 2, pp. 237/242 (1981). FIG. 24 is a schematic diagram showing the principle of the conventional foreign particles inspection method. Reference numeral 201 designates an object substrate to be inspected. In FIG. 24, a plane perpendicular to the surface of the drawing sheet, which includes the object substrate 201, is defined to be a principal plane of the object substrate 201. Reference numeral 202 designates a pattern on the object substrate 201. Reference numeral 203 designates foreign particles on the object substrate 201. Reference numeral 205 designates an s-polarized laser light source which supplies illumination in a direction approximately parallel to the principal plane of the object substrate 201 (the term "s-polarized" refers to a polarized light perpendicular to the sheet surface). Reference numeral 206 designates an objective lens having an optical axis substantially perpendicular to the principal plane of the object substrate 201. Reference numeral 207 is an analyzer set to transmit a p-polarized light (polarized light parallel to the sheet surface), 208 designates an image forming lens, and 209 designates a photoelectric conversion element.

Operation of the above described prior art arrangement for substrate inspection will be explained. When light is emitted onto the object substrate 201 from the s-polarized laser light source 205 in a direction generally parallel to the surface of the object substrate 201, reflected light 210 from the pattern 202 is reflected without being subject to any disturbance in its direction of polarization. In other words, reflected light 210 will be s-polarized light and will pass through the objective lens 206 and be shielded by the analyzer 207. The analyzer will shield the light because it is set to transmit p-polarized light, i.e., to shield s-polarized light. When foreign particles 203 are illuminated with light from the s-polarized laser light source 205, scattering of light occurs due to the foreign particles 203 and the polarized component of the light is disturbed. Therefore, the light is turned into scattered light 211 and includes a p-polarized light component. The scattered light 211, after passing through the objective lens 206, has its s-polarized light component shielded by the analyzer 207 so that only the p-polarized light component is allowed to pass through the analyzer 207. The light is then formed into an image on the photoelectric conversion element 209 by the image forming lens 208. An output signal from the photoelectric conversion element 209 makes it possible to detect the position at which the foreign particles are present.

With the above described arrangement, however, while the p-polarized light component of reflected light 210 from the pattern 202 is completely reduced to zero on the optical axis of the objective lens 206, any reflected light ray which makes an angle with the optical axis has a p-polarized light component. If the reflectivity of light from the pattern is large, it is a source of a large amount of noise.

The intensity of scattered light 211 from the foreign particles 203 becomes lower in proportion as the foreign particles 203 are smaller in size. In FIG. 24, it is assumed that the angle between the light from the laser light source 205 and the optical axis of the objective lens 206 is a detection angle θ. The intensity of the p-polarized light component of the scattered light 211 from the foreign particles 203 detected by the photoelectric conversion element 209 is S (signal), and the intensity of p-polarized light component of the reflected light 210 from a pattern 202 (such as aluminum wiring, which is of larger reflectivity) is N (noise). With the detection angle θ taken on the axis of abscissa, signal-to-noise ratio S/N values are as shown in FIG. 25. As is apparent from FIG. 25, when the detection angle=90° as in the prior art, the S/N value is less than 1 and foreign particles 203 cannot be distinguished from the pattern 202.

Another example of a prior art arrangement is described in U.S. Pat. 5,127,726. In this prior art arrangement, laser light is directed toward the inspection surface of an object at a relatively low angle so as to enable detection to be made at a position which makes an acute angle with the inspection surface. However, when laser light is projected from a position which is about 10° or more away from the inspection surface, the N (noise) component of the reflected light from the pattern is considerably large. In this example, the value of the signal-to-noise ratio S/N is so small that foreign particles cannot be distinguished from the pattern.

In the prior art methods, when the reflectivity of the pattern is high and the intensity of reflected light from the pattern is high, or when the foreign particles are small and the reflected light from the foreign particles is of low intensity, the foreign particles cannot be distinguished from the pattern.

SUMMARY OF THE INVENTION

An object of the present invention is to provide a method and an apparatus for foreign particle inspection which can greatly enhance the intensity of detection light from foreign particles relative to the intensity of detection light from the pattern. The present invention can enhance the distinction between the foreign particles and the pattern, and enable the detection of even very minute foreign particles.

The first aspect of the present invention is a method for inspecting foreign particles and includes illuminating an inspection surface with a beam which is either s-polarized or p-polarized. The axis of the illuminating light is generally parallel to the inspection surface or intersects the inspection surface at an angle which is greater than or equal to 1° and less than 5°. The optical axis used for detection is set at an acute angle with respect to the inspection surface and at an angle of 30° or less with respect to the illumination beam. The portion of light detected is the portion having a polarity opposite to the polarity of the inspecting light. For example, when s-polarized light is used for the inspecting light, the detected light is the p-polarized light reflected from the surface or particles thereon. More specifically, in illuminating the object, laser beams from a laser light source are passed through a collimator lens so as to produce parallel beams. Only one polarization of light, for example, an s-polarized light, is allowed to pass by a polarizer. A cylindrical lens directs the light beams so as to illuminate a line-form region on the inspection surface of the inspection object at an incident angle which is greater than or equal to 1° and less than 5°. At such a small angle, the light beams are substantially parallel to the inspection object. The s-polarized laser beam is reflected by a pattern on the surface of the inspection object or scattered by foreign particles on that surface. Of the reflected light, only the light of opposite polarization, i.e., p-polarized light, is transmitted by an analyzer. This p-polarized laser light, which indicates foreign particles, is passed through an objective lens. The p-polarized laser light is focussed by an image forming lens onto a line sensor. The p-polarized laser light is then photoelectrically converted into a detection signal by the line sensor. A high precision detection is made of the foreign particles through the resulting detection signal.

The apparatus of the present invention includes an illumination device arranged so as to define an optical axis that is substantially parallel to an inspection surface of an inspection object. The illumination device directs a polarized beam, for example, an s-polarized beam, toward the inspection surface. The apparatus includes a detection device oriented so as to have an optical axis at an acute angle with respect to the inspection surface at an angle of 300 or less with respect to the optical axis of the illumination device. The detection device detects a light component from the reflected light and the scattered light which has a polarization opposite to that of the illuminating light, i.e., p-polarized light. The detection device also performs photoelectric conversion of the light component. The apparatus also includes a signal processing unit for detecting foreign particles based on a signal from the photoelectric conversion of the detection device.

The incident light propagates in an incident plane which is substantially parallel to the inspection surface. S-polarized light is light that has an electric vector component that oscillates in a direction that is substantially perpendicular to the incident plane.

P-polarized light is light that has an electric vector component that oscillates within the incident plane.

Detection angle θ, which is the angle between an optical axis at a detection side and the inspection surface, is less than 90°.

The differential angle is the angle between projections onto the inspection surface of the incident optical axis and the detection optical axis. This angle is set to be 0°–30°.

The inspection surface of the inspection object is illuminated with a beam which is an s-polarized light in such a manner that the optical axis of the illumination is generally parallel to the inspection surface of the object or intersects the inspection surface at a small angle. The optical axis also makes a differential angle of 30° or less with respect to the optical axis of the detection beam. Detection is accomplished by detecting the p-polarized component of the reflected light and the scattered light. In this way, the intensity of detection light from the foreign particles can be noticeably improved over the intensity of detection light from the pattern or the like. This results in an improvement in the distinction between the foreign particles and any light component, i.e., noise, from the pattern. The present invention thereby enables detection of even very minute foreign particles. Alternatively, a p-polarized light beam can be used as the illumination beam and an s-polarized light beam can be used as the detection beam.

BRIEF DESCRIPTION OF THE DRAWINGS

These and other aspects and features of the present invention will become clear from the following description taken in conjunction with the preferred embodiments thereof with reference to the accompanying drawings, in which.

DETAILED DESCRIPTION OF THE PREFERRED EMBODIMENTS

Figure 1:
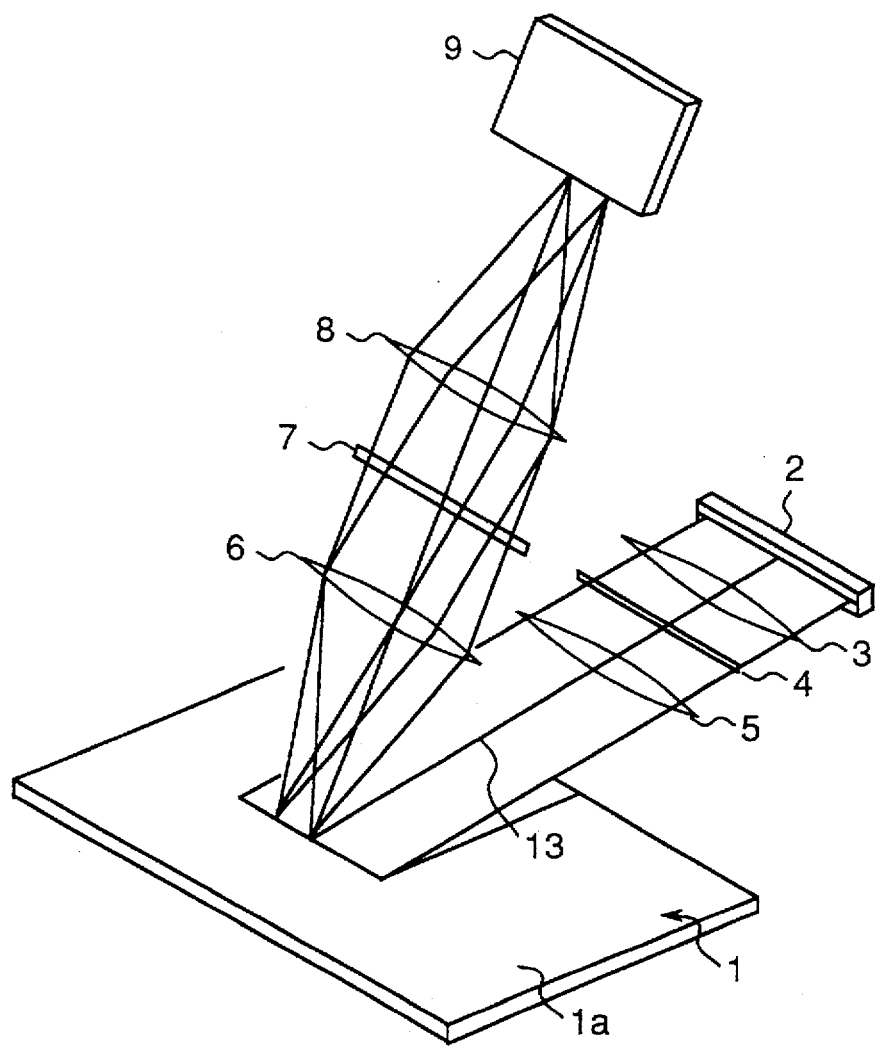
FIG. 1 is a schematic diagram showing a first embodiment of the invention.

Throughout the accompanying drawings, like parts are designated by like reference numerals.

FIG. 1 is a schematic diagram of a first embodiment of the present invention.

Figure 2:
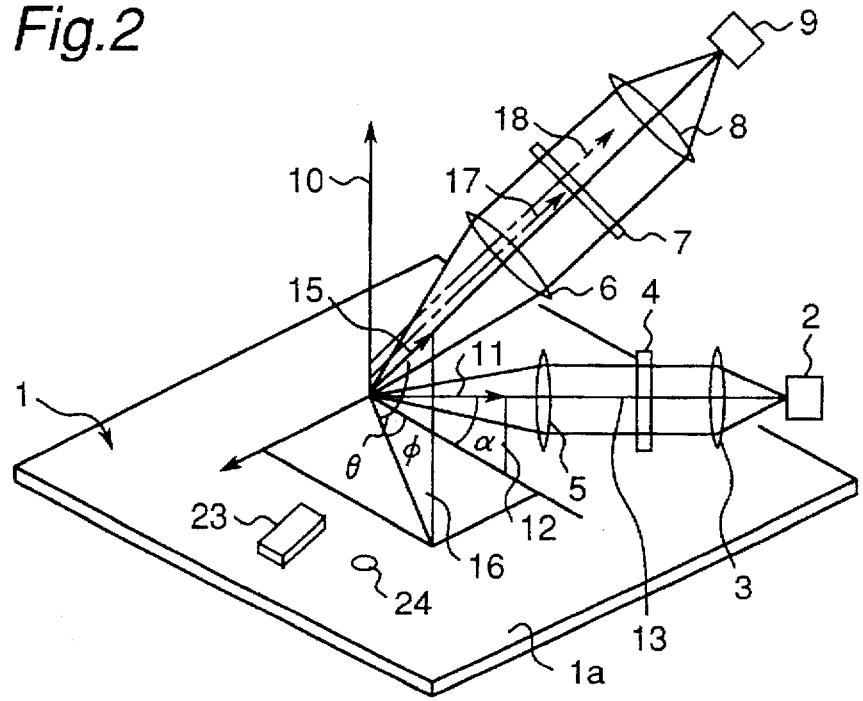
FIG. 2 is a explanatory diagram of the first embodiment.
Figure 3:
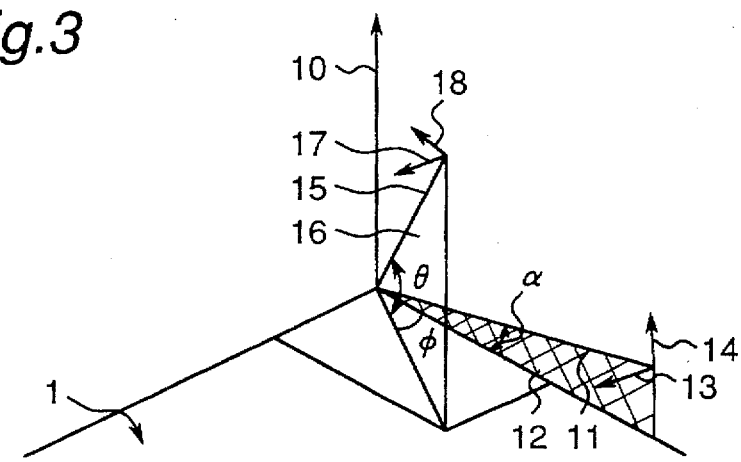
FIG. 3 is an explanatory diagram of the vectors of the light beams of the first embodiment.

FIG. 2 is an explanatory view of FIG. 1, and FIG. 3 is an explanatory diagram of the light vectors shown in FIG. 2.

In the drawings, reference numeral 1 designates a substrate which is subject to inspection, hereafter called an inspection object; 2 designates a laser light source; 3 designates a collimator lens for collimating light rays from the laser light source; 4 designates a polarizer; and 5 designates a cylindrical lens for causing parallel light rays to be formed into a line-form image. The cylindrical lens 5 has a rear focal plane located on the surface of the inspection object. Reference numeral 6 designates an objective lens having a front focal plane lying on the same location as that of the rear focal plane of the cylindrical lens 5. Reference numeral 7 designates an analyzer; 8 designates an image forming lens; and 9 designates a line sensor disposed on the image forming plane of the image forming lens 8.

Reference numeral 10 designates a vector which is normal to the inspection surface 1a of the inspection object 1. Reference numeral 11 designates a vector representative of light in the direction of incidence which lies on an optical axis shared by the laser light source 2, collimator lens 3 and cylindrical lens 5. An angle of incidence a, which is the angle between the incident direction vector 11 and the surface of the inspection object 1, is set to about 0°. Reference numeral 12 designates a plane of incidence defined by the normal vector 10 and the incident direction vector 11. As FIG. 3 shows, reference numeral 13 designates an s-polarized laser light having an electric field vector component which vibrates perpendicularly with respect to the plane of incidence 12. Reference numeral 14 designates a p-polarized laser light having an electric field vector component which vibrates within the plane of incidence 12. The polarizer 4 is designed to transmit s-polarized laser light 13 only. Reference numeral 15 designates a detection direction vector which represents the optical axis of the objective lens 6 and image forming lens 8. The detection is accomplished on or about, i.e., oriented generally around, this optical axis. The detection angle θ, which is the angle between the detection direction vector 15 and the surface of the inspection object 1, is set to be an acute angle. An orientation angle (differential angle) φ is the angle between projections onto the surface of the inspection object of the incident direction vector 11 and the detection direction vector 15. The orientation angle φ is set to be 0°–30°. Reference numeral 16 designates a detection plane defined by the normal vector 10 and the detection direction vector 15. Reference numeral 17 designates an s-polarized laser light having an electric field vector component that oscillates perpendicularly with respect to the detection plane 16. Reference numeral 18 designates a p-polarized laser light having an electric field vector component that oscillates within the detection plane 16. The analyzer 7 is designed to transmit p-polarized laser light 18 only.

The operation of the first embodiment of the present invention is as follows. Laser beams from the laser light source 2 are passed through the collimator lens 3 producing parallel beams. The polarizer 4 is oriented so as to allow passage of the s-polarized laser beam 13 on the incident plane 12. The cylindrical lens 5 directs the light beams so as to illuminate a line-form region on the surface of the inspection object 1 at an incident angle α which is substantially parallel to the inspection object 1. The s-polarized laser beam 13 on the incident plane 12 is reflected from a pattern 23 on the surface of the inspection object 1 or is scattered by foreign particles 24 on the surface of the inspection object.

Figure 4:
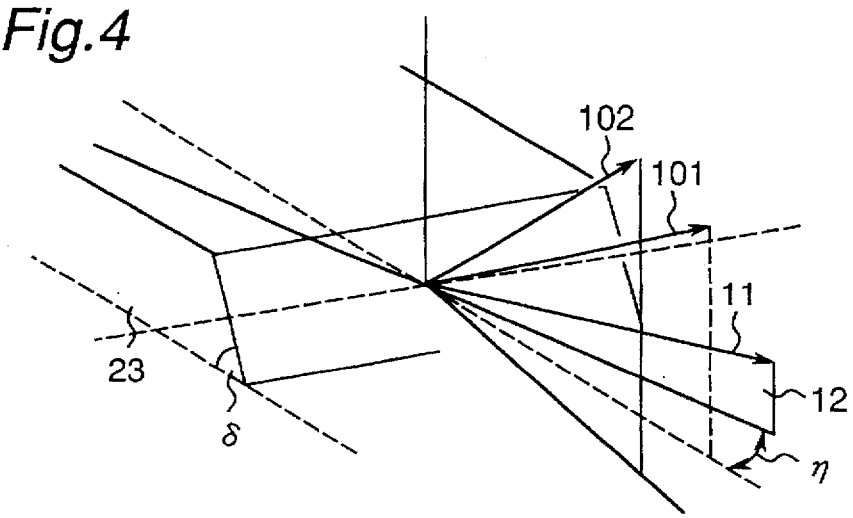
FIGS. 4 and 5A are explanatory diagrams showing light rays reflected from a pattern of the object being inspected by the first embodiment.
Figure 5A:
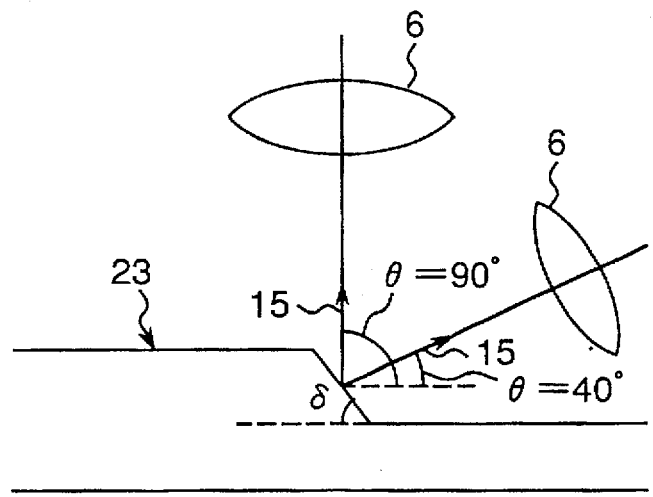
Figure 5B:
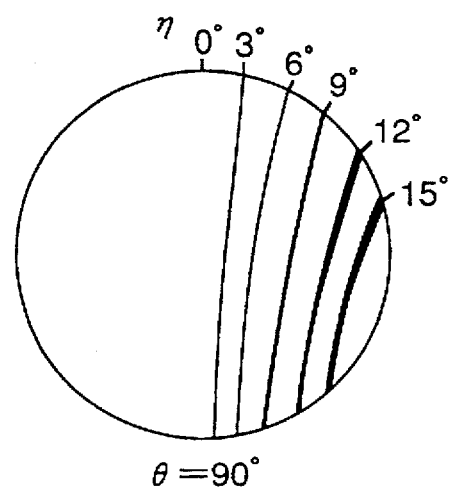
FIGS. 5B and 5C are diagrams showing the intensity profile of light reflected from a pattern of the object being inspected by the first embodiment.
Figure 5C:
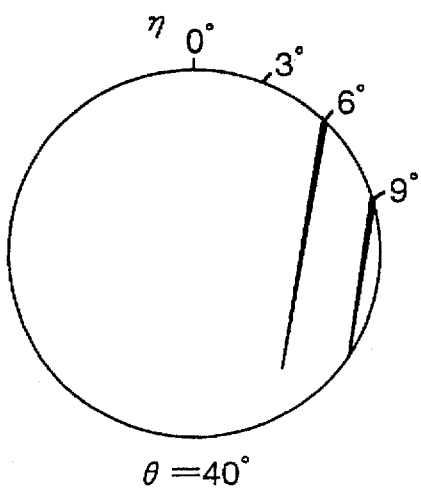

FIG. 4 shows a reflected light vector 102 representing light rays reflected from the pattern 23 on the object substrate 1. Assuming that the pattern 23 is a set of many minute planes, reflected light vectors 102 may be considered for such individual planes. Vector 102 is ultimately determined on the basis of the incident direction vector 11 and a normal vector 101 which lies on a minute plane defined by normal vector 101 and normal vector 10. Since the normal vector 101 is defined by the angle η between the minute plane and incident plane 12 and the gradient δ, the direction of the reflected light vector 102 is defined based on the gradient δ of the reflecting plane and the angle η between that plane and the incident plane 12. Figs. 5A, 5B and 5C show the angles η and the intensities of the p-polarized components of the reflected light from the pattern 23 that enter the objective lens 6 of the detection system for certain detection angles θ.

More specifically, in FIGS. 5B and 5C, at an angle η between the minute plane (a component plane of the pattern 23) and the incident plane 12, changes in the position of the incident light are shown when the gradient δ of the minute plane is successively varied between 0° and 90°. As shown, lines are depicted thicker in proportion to increasing intensity of incident light. It can be seen from the figure that where detection angle θ=90°, the range of incident angles η is relatively large, while where detection angle θ=40°, the range of incident angles η is relatively small. In the vicinity of θ=0°, there will occur little or no p-polarized light component, and therefore, the intensity of incident light is very low. If the detection angle θ is set lower, the p-polarized light component of reflected light from the pattern 23 on the object substrate 1 is very weak.

Figure 6:
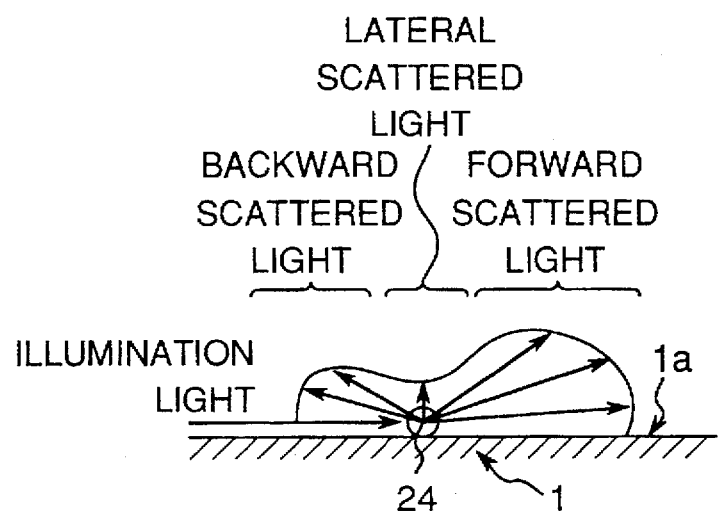
FIG. 6 is a diagram showing the intensity profile of scattered light rays due to foreign particles in the operation of the first embodiment.

Laser light rays scattered by minute foreign particles 24 have an intensity distribution as shown in FIG. 6. Of the scattered light rays, backward scattered light rays are partially incident on the aperture of the objective lens 6 of the detection device. The scattered rays from a foreign particle, as shown, have a higher intensity in the forward and backward directions than in the lateral direction, and therefore, these forward and backward rays provide a higher signal intensity than the lateral scattered rays which are detected when the detection direction vector 15 is set at or about the lateral direction.

Only p-polarized laser light 18 from the detection plane 16 is transmitted by the analyzer 7 and is focussed by the image forming lens 8 on the line sensor 9. The p-polarized laser light 18 from the detection plane 16 is photoelectrically converted by the line sensor 9. This permits a high precision detection of foreign particles through the resulting detection signal.

The reasons for using an s-polarized laser beam 13 are as follows.

In Table 1, wherein incident angle α=2°, detection angle θ=30° and the orientation angle φ=0°, an experimental comparison of results is shown between two scenarios. The first scenario involves the use of s-polarized light 13 in the incident plane 12 for the illumination of the foreign particles 24 and the use of p-polarized light 18 in the detection plane for the detection of the foreign particles 24. The second scenario involves the use of p-polarized light 14 in the incident plane for the illumination, and the use of s-polarized light 17 in the detection plane for the detection. It is noted that the respective illumination light rays are of the same intensity. The results are represented by values represented with respect to the reference value in the Table.

TABLE 1

| | Illuminate with s-polarized laser light in incident plane Detect with p-polarized laser light in detection plane | Illuminate with p-polarized laser light in incident plane Detect with s-polarized laser light in detection plane |
|---|---|---|
| Foreign particles signal | 5 | 6 |
| Noise from pattern | 1 (Reference value) | 3 |
| Foreign particles detection S/N | 5 | 2 |

As is apparent from Table 1, when the s-polarized laser light 13 in the incident plane 12 is used for illumination, with the p-polarized laser light 18 in the detection plane 16 being used for inspection, detection of the foreign particles 24 is easier because of the higher S/N (signal-to-noise ratio).

The quantity of signals received from the foreign particles 24 is so large that the light source power may be reduced. It is thus possible to utilize a less expensive, low-power laser.

The quantity of the signals received from the foreign particles 24 is so large that a signal-to-noise ratio of a reasonable level can be obtained even if the NA (number of aperture) of the objective lens 6 is reduced. Therefore, by increasing the focal depth of the detection device, it is possible to eliminate the effect of defocussing due to surface irregularity of the object substrate.

The fact that a better signal-to-noise ratio can be obtained enables greater simplicity in construction compared to conventional systems. This in turn provides for both size and cost reduction and also for improved reliability.

One example of a prior art method is described in the Japanese academic publication "Keisoku Jido Seigyo Gakkai Ronbunshu," Vol. 25, No. 9, pp. 954/961 (1989). According to the teaching of this publication, quantities of reflected rays, produced from two kinds of illuminations of different incident angles, are used to detect foreign particles. Another example of a prior art method is found in the Japanese publication "Keisoku Jido seigyo Gakkai Ronbunshu," Vol. 17, No. 2, pp. 237/242 (1981). According to the teaching of this publication, quantities of reflected rays produced from two to four separate illuminations of the same incident angle but from different directions are used for detecting foreign particles.

A number of variations can be made to the above described embodiment of the present invention. For example, a photoelectric conversion element, such as a photodiode or photomultiplier, may be used instead of the line sensor 9. A slit arrangement can be used to provide a line-form illumination rather than the cylindrical lens 5.

In the above described embodiment, the orientation angle $\phi$ is 0°. However, the angle need not be so limited. An orientation angle of 30° or less would be acceptable. It is preferable that the orientation angle $\phi$ is 15° or less when a line sensor is not used for detection. When the line sensor is used for detection, an orientation angle $\phi$ of 0° is preferable because it is easy to carry out optical adjustment at such an angle.

In the above described embodiment, the optical system of the detection device includes the objective lens 6, analyzer 7 and imaging lens 8. Needless to say, however, the optical system may consist essentially of the objective lens and analyzer.

Figure 7:
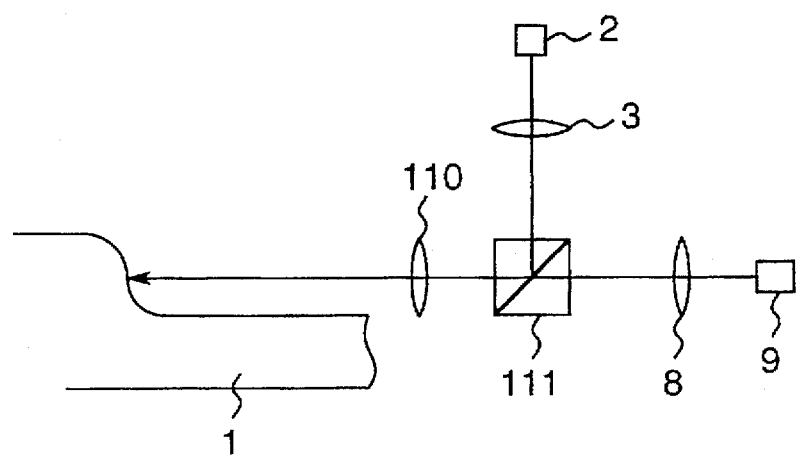
FIG. 7 is a schematic diagram showing one aspect of the operation of the first embodiment in which a detection angle is 0°.

FIG. 7 illustrates another configuration of the first embodiment of the invention. The configuration of FIG. 7 uses a detection angle $\theta=0°$ at which the illumination system and the detection system may spatially interfere with each other. Laser light emitted from the laser source 2 passes through the collimator lens 3, a polarized beam splitter 111, and an objective lens 110 before it is projected as a line-form beam onto the inspection object 1. The azimuth or orientation of the polarized beam splitter 111 is set so that only s-polarized light, which has an electric field vector perpendicular to the plane of incidence of the light, is bent so as to be projected onto the inspection object 1. Light rays which are scattered by foreign particles on the inspection object 1, and/or which are reflected by the pattern, are collected by the objective lens 110. Only a p-polarized light component of the light rays is transmitted by the polarized beam splitter 111 which is set as described above. The light rays are then imaged on the line sensor 9 by the imaging lens 8.

In this way, the optical axes of both the illumination system and the detection system can be brought close to each other by the polarized beam splitter 111. Further, the polarized beam splitter 111 can perform the functions of both polarizer 4 of the illumination system and analyzer 7 of the detection system, whereby the same performance as that of the FIG. 2 embodiment can be obtained. Therefore, it is possible to set the detection angle $\theta$ at 0° or more.

Figure 8:
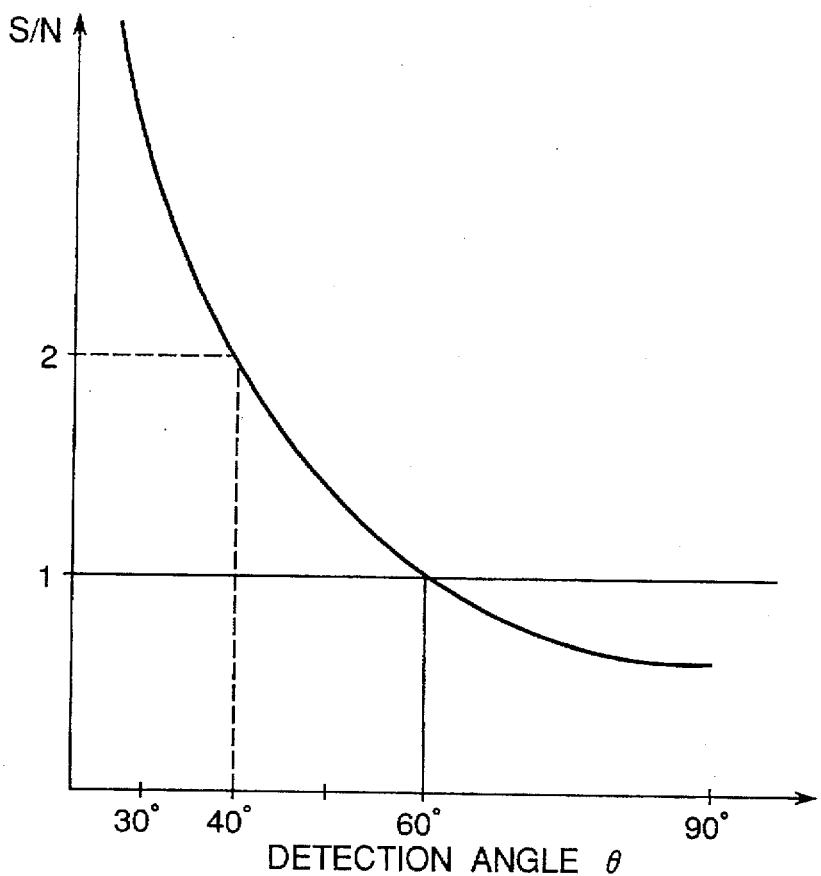
FIG. 8 is a graph showing the relationship between detection angle and the signal-to-noise ratio S/N in the operation of the first embodiment.

Next, the reason why the detection angle $\theta$ is preferably set to less than 60° will be explained. In FIG. 8, the signal S is the intensity of the p-polarized component of scattered light rays from the foreign particles 24 detected by the line sensor 9. The noise N is the intensity of the p-polarized component of the reflected light from the pattern 23. Pattern 23 is made of a material such as aluminum wiring that has a large reflectivity characteristic. Measurements of values of the signal-to-noise ratio S/N are shown in FIG. 8, with detection angle $\theta$ taken on axis of abscissa.

Since it is necessary that the S/N value be more than 1 in order to detect foreign particles, as indicated by the measurements, the detection angle $\theta$ must be less than 60°. It is most preferable that the detection angle $\theta$ is 30° when the line sensor is used.

The reason why the incident angle $\alpha$ should be within the range of $1°\leq\alpha<5°$ will be explained below.

Figure 9:
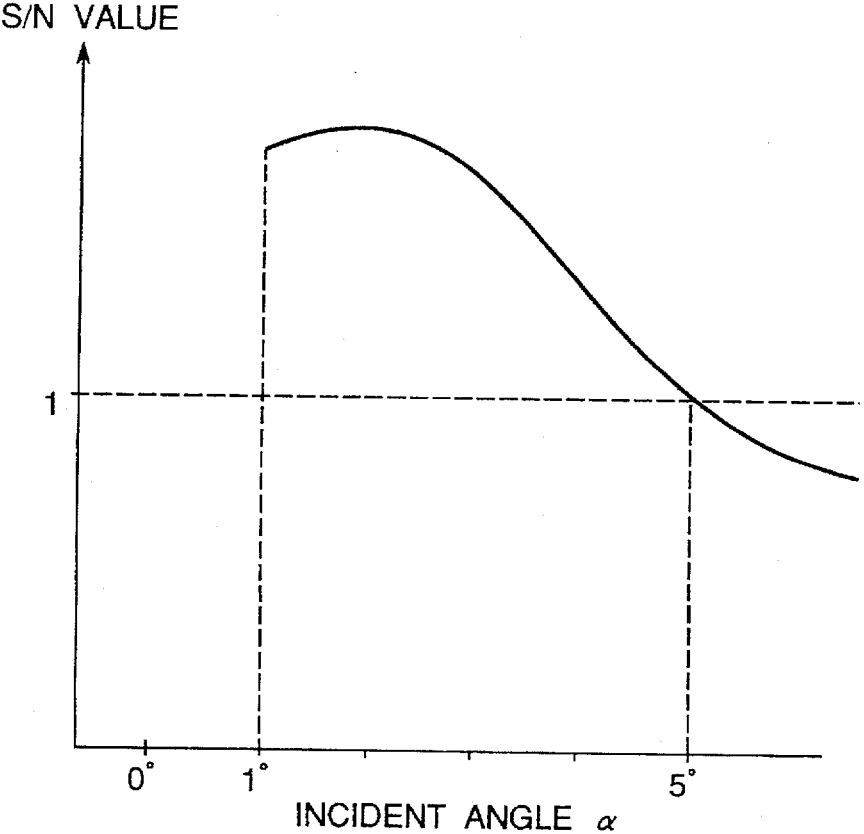
FIG. 9 is a graph showing the relationship between incident angle and the signal-to-noise ratio S/N in the operation of the first embodiment.

FIG. 9 is a graph illustrating measurements of the signal-to-noise ratio S/N for a range of incident angles $\alpha$, with the detection angle $\theta$ set at 40°. Where the incident angle $\alpha$ is less than 1°, the detection is difficult. In addition, the laser beam may become incident on the edge of the sample causing a substantial increase in the noise component. Where the incident angle $\alpha$ is equal to or greater than 5°, the S/N value is equal to or lower than 1 as shown. In such a situation, the noise component is so large that the foreign particles cannot be detected. Therefore, it is preferable that the incident angle $\alpha$ be set within the range of greater than or equal to 1° and less than 5°, i.e., $1°\leq\alpha<5°$. It is preferable that the incident angle $\alpha$ is set to be greater than or equal to 1° and less than 3°. It is most preferable that the incident angle $\alpha$ is 2° when the line sensor is used.

Figure 10:
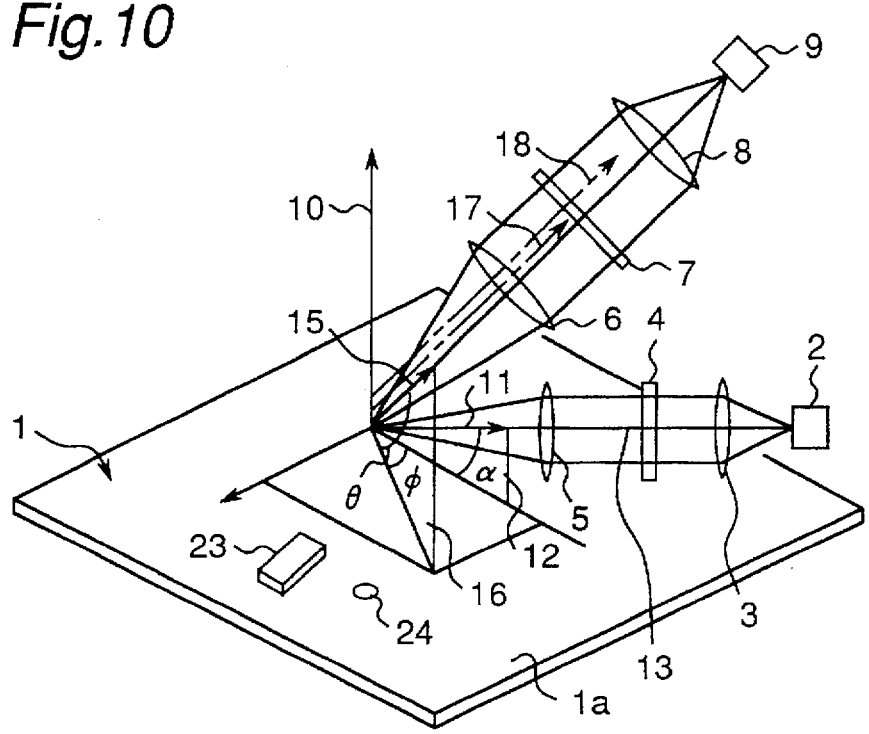
FIG. 10 is a schematic diagram showing a second embodiment of the invention.

FIG. 10 shows the basic configuration of the second embodiment of the invention. In FIG. 10, elements identical to those in FIG. 2 are designated by like numerals. The second embodiment differs from the first embodiment in that the range of the detection angles $\theta$ is 0°–40°. Operation of the second embodiment is similar to the operation of the first embodiment.

Figure 11:
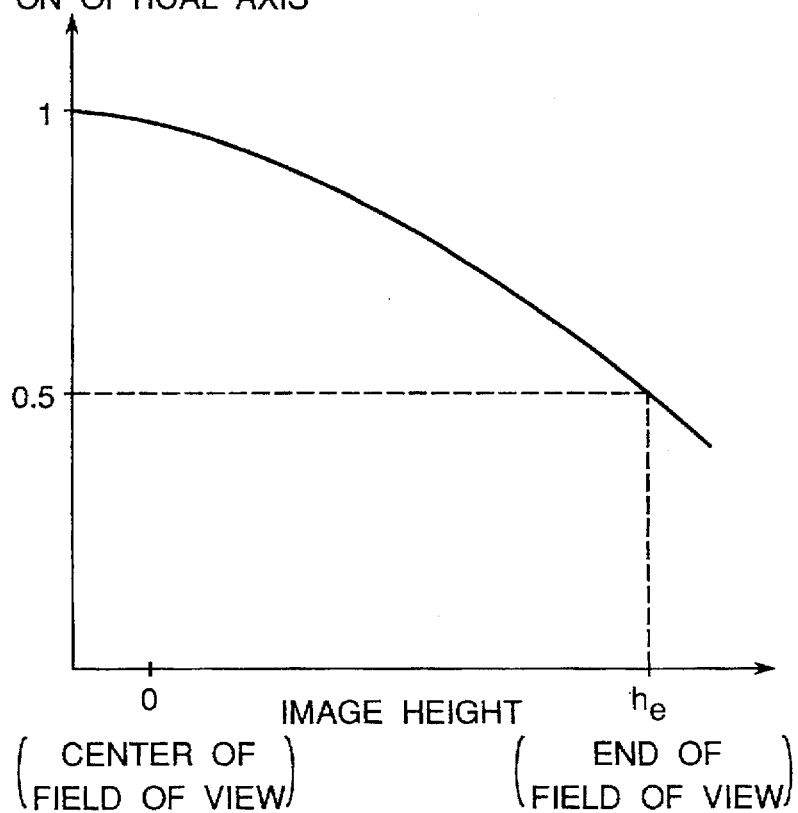
FIG. 11 is a graph showing the relationship between distance from optical axis and the signal-to-noise ratio S/N in the operation of the second embodiment.
Figure 12:
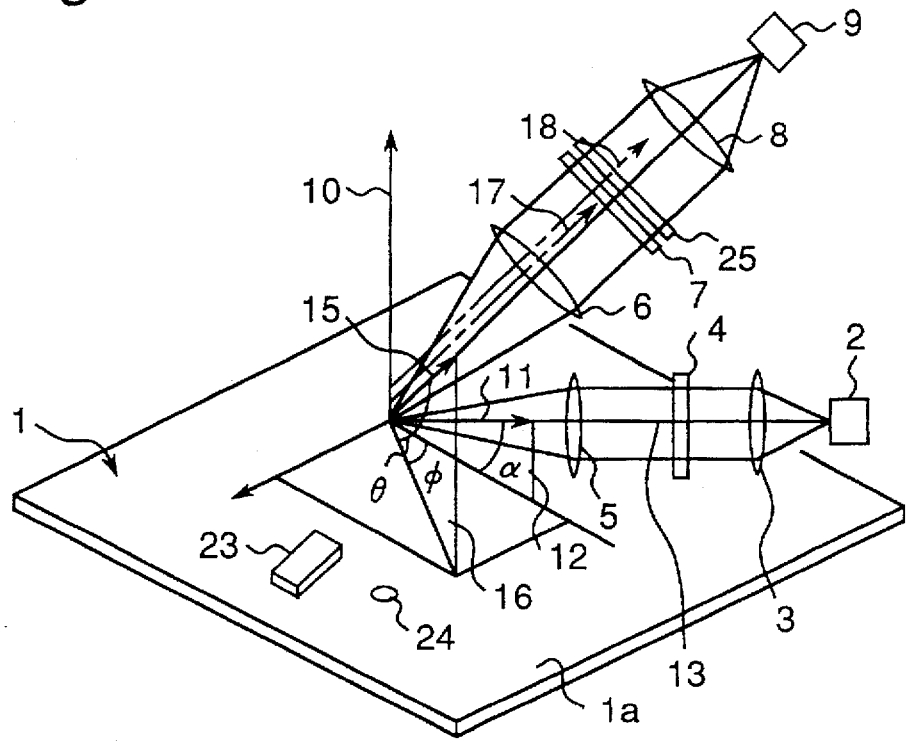
FIG. 12 is a schematic diagram showing a third embodiment of the invention.
Figure 13:
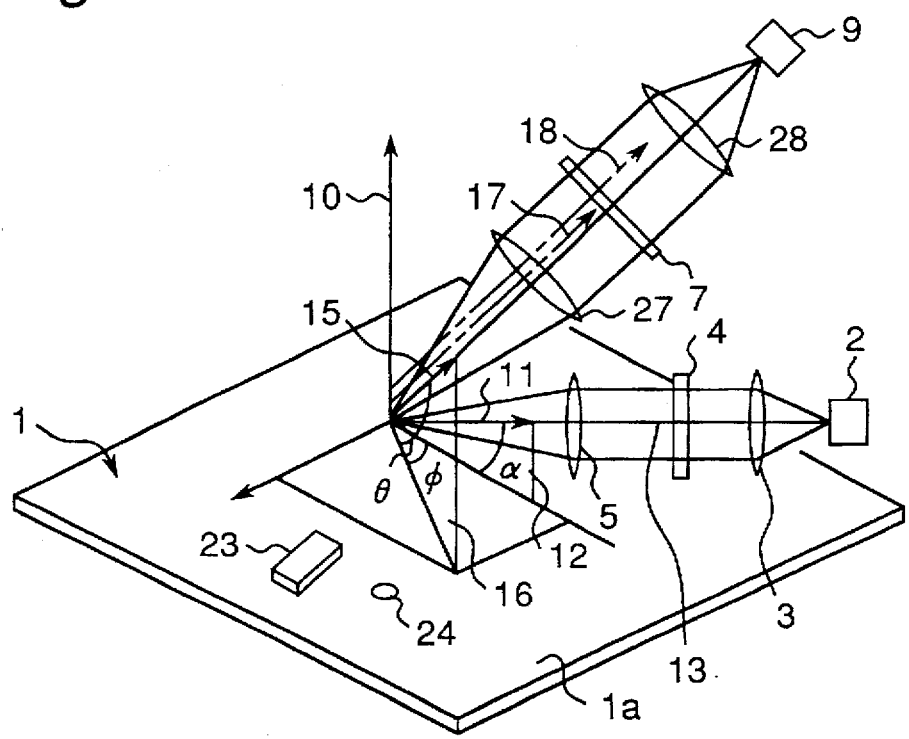
FIG. 13 is a schematic diagram showing a fourth embodiment of the invention.

The reason why the detection angle $\theta$ is equal to or lower than 40° is as follows. First, consider the S/N value for the field of view as a whole. FIG. 11 shows the S/N values FIG. 1 is a schematic diagram of a first embodiment of the present invention.

FIG. 2 is an explanatory view of FIG. 1, and FIG. 3 is an explanatory diagram of the light vectors shown in FIG. 2.

In the drawings, reference numeral 1 designates a substrate which is subject to inspection, hereafter called an inspection object; 2 designates a laser light source; 3 designates a collimator lens for collimating light rays from the laser light source; 4 designates a polarizer; and 5 designates a cylindrical lens for causing parallel light rays to be formed into a line-form image. The cylindrical lens 5 has a rear focal plane located on the surface of the inspection object. Reference numeral 6 designates an objective lens having a front focal plane lying on the same location as that of the rear focal plane of the cylindrical lens 5. Reference numeral 7 designates an analyzer; 8 designates an image forming lens; and 9 designates a line sensor disposed on the image forming plane of the image forming lens 8.

Reference numeral 10 designates a vector which is normal to the inspection surface 1a of the inspection object 1. Reference numeral 11 designates a vector representative of light in the direction of incidence which lies on an optical axis shared by the laser light source 2, collimator lens 3 and cylindrical lens 5. An angle of incidence a, which is the angle between the incident direction vector 11 and the surface of the inspection object 1, is set to about 0°. Reference numeral 12 designates a plane of incidence defined by the normal vector 10 and the incident direction vector 11. As FIG. 3 shows, reference numeral 13 designates an s-polarized laser light having an electric field vector component which vibrates perpendicularly with respect to the plane of incidence 12. Reference numeral 14 designates a p-polarized laser light having an electric field vector component which vibrates within the plane of incidence 12. The polarizer 4 is designed to transmit s-polarized laser light 13 only. Reference numeral 15 designates a detection direction vector which represents the optical axis of the objective lens 6 and image forming lens 8. The detection is accomplished on or about, i.e., oriented generally around, this optical axis. The detection angle θ, which is the angle between the detection direction vector 15 and the surface of the inspection object 1, is set to be an acute angle. An orientation angle (differential angle) φ is the angle between projections onto the surface of the inspection object of the incident direction vector 11 and the detection direction vector 15. The orientation angle φ is set to be 0°–30°. Reference numeral 16 designates a detection plane defined by the normal vector 10 and the detection direction vector 15. Reference numeral 17 designates an s-polarized laser light having an electric field vector component that oscillates perpendicularly with respect to the detection plane 16. Reference numeral 18 designates a p-polarized laser light having an electric field vector component that oscillates within the detection plane 16. The analyzer 7 is designed to transmit p-polarized laser light 18 only.

The operation of the first embodiment of the present invention is as follows. Laser beams from the laser light source 2 are passed through the collimator lens 3 producing parallel beams. The polarizer 4 is oriented so as to allow passage of the s-polarized laser beam 13 on the incident plane 12. The cylindrical lens 5 directs the light beams so as to illuminate a line-form region on the surface of the inspection object 1 at an incident angle α which is substantially parallel to the inspection object 1. The s-polarized laser beam 13 on the incident plane 12 is reflected from a pattern 23 on the surface of the inspection object 1 or is scattered by foreign particles 24 on the surface of the inspection object.

FIG. 4 shows a reflected light vector 102 representing light rays reflected from the pattern 23 on the object substrate 1. Assuming that the pattern 23 is a set of many minute planes, reflected light vectors 102 may be considered for such individual planes. Vector 102 is ultimately determined on the basis of the incident direction vector 11 and a normal vector 101 which lies on a minute plane defined by normal vector 101 and normal vector 10. Since the normal vector 101 is defined by the angle η between the minute plane and incident plane 12 and the gradient δ, the direction of the reflected light vector 102 is defined based on the gradient δ of the reflecting plane and the angle η between that plane and the incident plane 12. Figs. 5A, 5B and 5C show the angles η and the intensities of the p-polarized components of the reflected light from the pattern 23 that enter the objective lens 6 of the detection system for certain detection angles θ.

More specifically, in FIGS. 5B and 5C, at an angle η between the minute plane (a component plane of the pattern 23) and the incident plane 12, changes in the position of the incident light are shown when the gradient δ of the minute plane is successively varied between 0° and 90°. As shown, lines are depicted thicker in proportion to increasing intensity of incident light. It can be seen from the figure that where detection angle θ=90°, the range of incident angles η is relatively large, while where detection angle θ=40°, the range of incident angles η is relatively small. In the vicinity of θ=0°, there will occur little or no p-polarized light component, and therefore, the intensity of incident light is very low. If the detection angle θ is set lower, the p-polarized light component of reflected light from the pattern 23 on the object substrate 1 is very weak.

Laser light rays scattered by minute foreign particles 24 have an intensity distribution as shown in FIG. 6. Of the scattered light rays, backward scattered light rays are partially incident on the aperture of the objective lens 6 of the detection device. The scattered rays from a foreign particle, as shown, have a higher intensity in the forward and backward directions than in the lateral direction, and therefore, these forward and backward rays provide a higher signal intensity than the lateral scattered rays which are detected when the detection direction vector 15 is set at or about the lateral direction.

Only p-polarized laser light 18 from the detection plane 16 is transmitted by the analyzer 7 and is focussed by the image forming lens 8 on the line sensor 9. The p-polarized laser light 18 from the detection plane 16 is photoelectrically converted by the line sensor 9. This permits a high precision detection of foreign particles through the resulting detection signal.

The reasons for using an s-polarized laser beam 13 are as follows.

In Table 1, wherein incident angle α=2°, detection angle θ=30° and the orientation angle φ=0°, an experimental comparison of results is shown between two scenarios. The first scenario involves the use of s-polarized light 13 in the incident plane 12 for the illumination of the foreign particles 24 and the use of p-polarized light 18 in the detection plane for the detection of the foreign particles 24. The second scenario involves the use of p-polarized light 14 in the incident plane for the illumination, and the use of s-polarized light 17 in the detection plane for the detection. It is noted that the respective illumination light rays are of the same intensity. The results are represented by values represented with respect to the reference value in the Table.

beams. The polarizer 4 is oriented so as to allow passage of the s-polarized laser beam 13 on the incident plane 12. The cylindrical lens 5 directs the light beams so as to illuminate a line-form region on the surface of the inspection object 1 at an incident angle α which is substantially parallel to the inspection object 1.

The light projected for illumination is reflected by the pattern 23 on the surface of the inspection object 1. Thus, the polarized component of the reflected light incident on the objective lens 27 is very slight due to the effect of a plane of the particular direction or the like as described in the first embodiment.

Light rays scattered by the foreign particles 24 are stronger and/or more numerous than the light from the pattern 23. Of such reflected light from the pattern 23 and scattered light from the foreign particles 24, the light entering the objective lens 27, is shielded by the analyzer 7 so that only the p-polarized laser light 18 in the detection plane 16 is transmitted by the analyzer 7. The transmitted light is imaged by the imaging lens 28 onto the line sensor 9.

The p-polarized laser light 18 in the detection plane 16 is photoelectrically converted by the line sensor 9 so that high precision detection of foreign particles 24 can be performed. The fourth embodiment differs from the first embodiment in that the S/N value obtainable outside the optical axis is improved.

Figure 14:
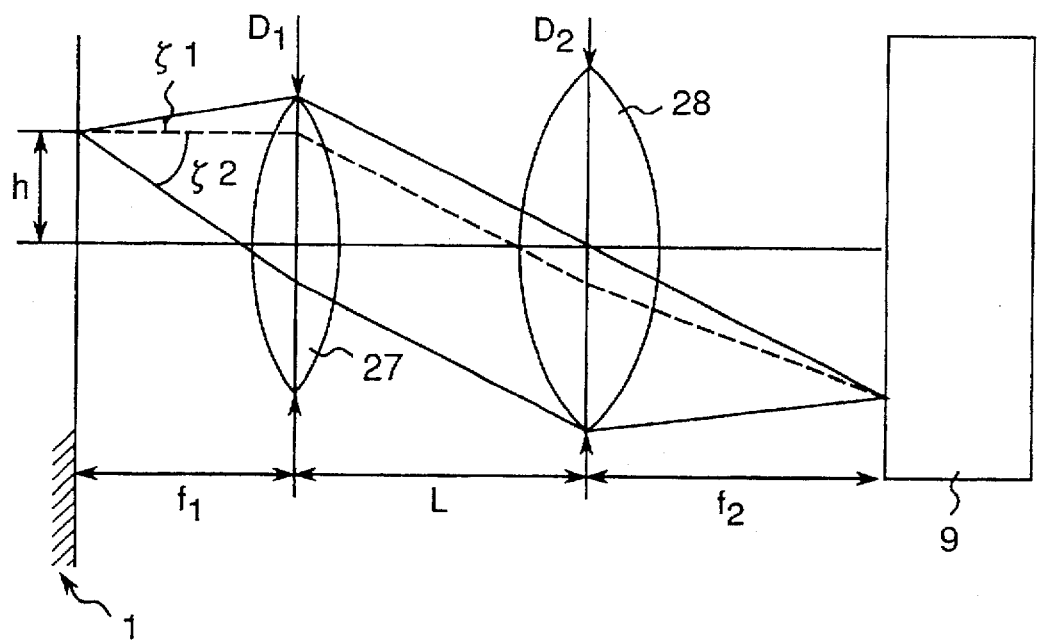
FIG. 14 is a diagrammatic view explanatory of the detection device in the fourth embodiment.

FIG. 14 is a view of the detection device as seen from above. In FIG. 14, light from the pattern 23 or the foreign particles 24 at a location away from the optical axis by a distance h can be imaged on the line sensor 9 as long as the light is within an angle range of $\zeta_1$ expressed by an equation (2):

$$\zeta_1 = \tan^{-1}\{(D_2/2-h)/f_1\} \quad (2)$$

The light can be imaged on the line sensor 9 if the light is within an angle range of $\zeta_2$ expressed by an equation (3):

$$\zeta_2 = \tan^{-1}\{(D_2/2+h=hL/f_1/f_1\} \quad (3)$$

As may be appreciated from equations (2) and (3), $\zeta_1$ is determined by the objective lens 27 only, whereas $\zeta_2$ is determined by the diameter $D_2$ of the imaging lens 28 and the distance L between the principal planes of the lenses.

In a direction outward from the optical axis, the angular range available for reception of light by the line sensor 9 is reduced. Correspondingly, the quantity of light from the foreign particles 24 is reduced.

The reflected light from the pattern 23, which is a specular reflection, is not distributed over the whole of the objective lens 27, but concentrates on a particular portion thereof. Therefore, despite the decrease in the angle available for light reception, there is no decrease in the intensity of the reflected light from the pattern 23. This poses an issue that the S/N value progressively decreases in a direction away from the optical axis. In order to resolve this issue, and so that as much scattered light as possible from the foreign particles 24 may be detected, the lenses are characterized such that the quantity of light which is shielded by the imaging lens 28 is not smaller than the quantity of light which is shielded by the objective lens 27. Where the maximal image height=A/2 wherein A denotes an inspection width, the lenses are characterized so as to satisfy the relation $\zeta_2 \geq \zeta_1$. By substituting the equations (2) and (3) for $\zeta_1$ and $\zeta_2$ in this relation, an equation (4) is obtained, which is identical with the equation (1).

$$D_2 D_1 = 2A + AL/f_1 \quad (4)$$

In consideration of the fact that there are often cases where the objective lens 27 and the imaging lens 28 are of the same diameter, and for the sake of simplicity of explanation, explanation is given below assuming that $D_1=D_2$. In this case, equation (4) may be rewritten as in equation (5).

$$2f_1 \geq L \quad (5)$$

The distance L, between the principal planes, is not more than two times the focal length $F_1$ of the objective lens 27.

Figure 15:
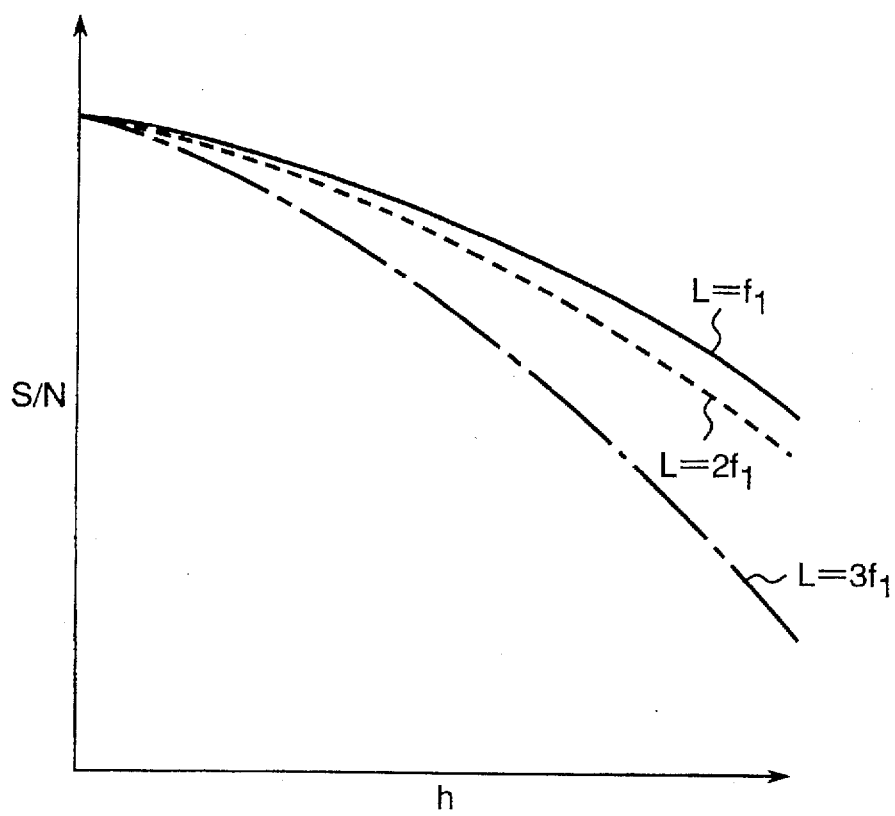
FIG. 15 is a graph showing the relationship between distance from optical axis and S/N in the operation of the fourth embodiment.

FIG. 15 shows computer-simulated S/N changes where $D_1=D_2$ and where the distance L between the principal planes and the distance h from the optical axis are changed in various ways. It can be appreciated from FIG. 15 that where $L \leq 2 f_1$, the decrease is S/N is relatively small. A more favorable S/N value can be obtained as compared with the case in which L is $2 f_1$ or more.

Thus, according to the fourth embodiment, by setting the imaging lens 28 in manner as indicated by the equation (4), it is possible to lower the rate of S/N decrease outside the optical axis.

As above described, according to the fourth embodiment, advantages similar to those provided by the first embodiment can be obtained. Further, according to the fourth embodiment, by setting the imaging lens 28 as taught by equation (4), it is possible to detect the foreign particles 24 with a high precision, even outside the optical axis.

A number of variations can be made to the fourth embodiment. For example, a photoelectric conversion element, such as a photodiode or photo-multiplier, may be used instead of the line sensor 9. A slit arrangement can be used to provide a line-form illumination ray rather than the cylindrical lens 5. When used in combination with any of the second and third embodiments, the fourth embodiment exhibits a greater precision of detection of the foreign particles.

Figure 16:
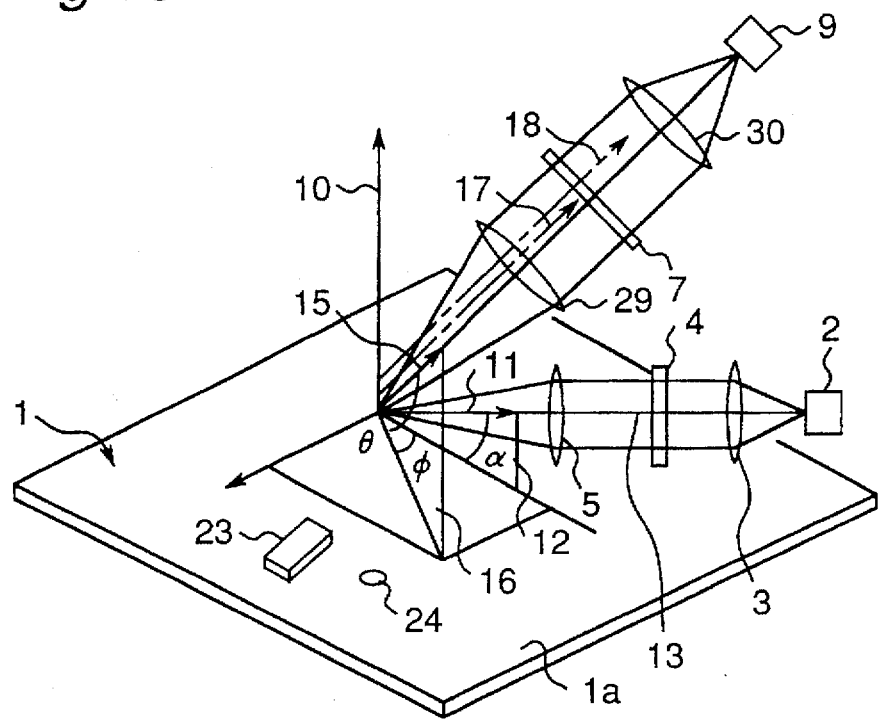
FIG. 16 is a schematic diagram showing a fifth embodiment of the invention.

FIG. 16 shows the basic configuration of the fifth embodiment of the invention. In FIG. 16, elements identical to those in FIG. 2 are designated by like numerals. The fifth embodiment differs from the first embodiment in that the objective lens 29 and the imaging lens 30 comprise a double-side telecentric optical system. Provision of such an optical system may be achieved, for example, by coinciding the front focal plane of the image-forming lens 30 and the rear focal plane of the objective lens 29.

In operation laser beams from the laser light source 2 are passed through the collimator lens 3 producing parallel beams. The polarizer −4 is oriented so as to allow passage of the s-polarized laser beam 13 in the incident plane 12. The cylindrical lens 5 directs the light beam so as to illuminate a line-form region on the surface of the inspection object 1 at an incident angle α which is substantially parallel to the inspection object 1.

The light projected for illumination is reflected by the pattern 23 on the surface of the inspection object 1. Thus, the polarized component of the reflected light incident on the objective lens 29 is very slight due to the effect of a plane of the particular direction or the like as described in the first embodiment.

Light rays scattered by the foreign particles 24 are stronger and more numerous than the light from the pattern 23. Of such reflected light from the pattern 23 and scattered light from the foreign particles 24, the light entering the objective lens 29, is shielded by the analyzer 7 so that only the p-polarized laser light 18 in the detection plane 16 is transmitted by the analyzer 7. The transmitted light is imaged by the image forming lens 30 onto the line sensor 9.

The p-polarized laser light 18 in the detection plane 16 is photoelectrically converted by the line sensor 9 so that high precision detection of the foreign particles 24 can be performed.

As above described, according to the fifth embodiment, advantages similar to those provided by the first embodiment can be obtained. Further, according to the fifth embodiment, the objective lens 29 and the image forming lens 30 comprise a double-side telecentric optical system and, therefore, even if some undulation occurs on the object substrate 1, no change occurs in the image magnification. This permits accurate measurement of the size of the foreign particles.

A number of variations can be made to the fifth embodiment. For example, a photoelectric conversion element, such as a photodiode or photo-multiplier, may be used instead of the line sensor 9. A slit arrangement can be used to provide a line-form illumination ray rather than the cylindrical lens 5. When used in combination with any of the second and third embodiments, the fifth embodiment exhibits greater precision detection of the foreign particles.

Figure 17:
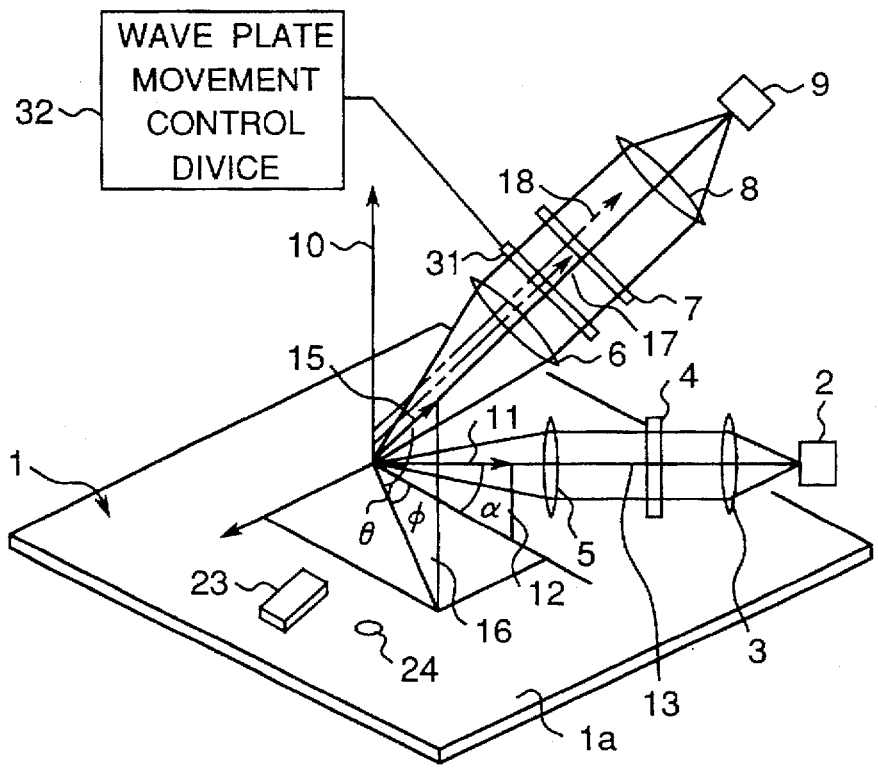
FIG. 17 is a schematic diagram showing a sixth embodiment of the invention.
Figure 18:
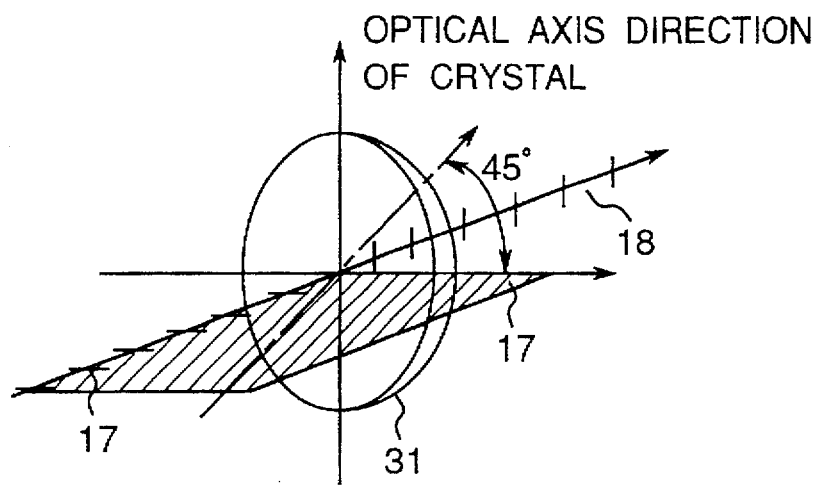
FIG. 18 is an explanatory diagram showing the disposition of a half-wave plate in the sixth embodiment.

FIG. 17 shows the basic configuration of the sixth embodiment of the invention. In FIG. 17, elements identical with those in FIG. 2 are designated by like numerals. The sixth embodiment differs from the first embodiment in that a half-wave plate 31, arranged between the objective lens 6 and the analyzer 7, and a wave plate movement control device 32, for controlling insertion and removal of the half-wave plate 31, are provided. As FIG. 18 shows, the angle between the optical axis of the crystal component of the half-wave plate 31 and the plane of polarization for the s-polarized laser light 17 in the detection plane 16 is set to about 45° so that the s-polarized laser light 17 can be converted into p-polarized light. Only the p-polarized laser light 18 is allowed to pass through the analyzer 7.

For explanation of the sixth embodiment, it is assumed that the inspection object is a substrate with no pattern formed thereon, or a substrate at an early stage of processing in which the pattern step difference of the substrate is still low. It is also assumed that the detection device has been fitted with the half-wave plate 31. Laser beams from the laser light source 2 are passed through the collimator lens 3 producing parallel beams. The polarizer 4 is oriented so as to allow passage of the s-polarized laser beam 13 in the incident plane 12. The cylindrical lens 5 directs the light beams so as to illuminate a line-form region on the surface of the inspection object 1 at an incident angle α which is substantially parallel to the inspection object 1.

The light thus projected for illumination is reflected by the pattern 23 on the surface of the inspection object 1. In the present case, it is assumed that the inspection object 1 is a substrate with a low pattern step difference. Naturally, therefore, the inspection object 1 includes only a very small pattern edge portion having only a small plane of reflection capable of incidence on the objective lens 6. Therefore, little or no reflected light from the pattern 23 is incident on the objective lens 6. Thus there is almost no noise with respect to the pattern 23.

Light rays scattered by the foreign particles 24 include both s-polarized laser light 17 and p-polarized laser light 18 in the detection plane 16.

The intensity of the s-polarized laser light 17 in the detection plane 16 is equal to or more than about five times the intensity of the p-polarized laser light 17 in the detection plane 16. After entering the objective lens 6, the reflected light, including such polarized light rays, is allowed to pass through the half-wave plate 31. The angle between the optical axis of the crystal component of the half-wave plate 31 and the plane of polarization for the s-polarized laser light 17 which is incident on the half-wave plate 31 is transmitted as a high-intensity p-polarized laser light 18, while the low-intensity p-polarized laser light 18 which is incident on the half-wave plate 31 is transmitted as a low-intensity s-polarized laser light 17.

Only the high intensity p-polarized laser light 18 is transmitted by the analyzer 7. Therefore, only the high intensity p-polarized light is imaged on the line sensor 9 by the image-forming lens 8. The p-polarized laser light 18 in the detection plane 16 is subjected to the photoelectric conversion by the line sensor 9 so that high precision detection of the foreign particles 24 can be performed. The sixth embodiment differs from the first embodiment in that when the inspection object 1 has no pattern formed thereon, or when the inspection object 1 is at an early stage of processing such that the pattern step difference of the substrate is still low, detection of the foreign particles 24 can be performed with greater sensitivity. Explanation will be given with respect to this point.

As compared with the intensity of the illumination of the s-polarized laser light 13 in the incidence plane 12, the intensity of the p-polarized laser light 18 on the detection plane 16 of back scattered rays produced from the foreign particles 24 is very low. As such, previously, the signal-to-noise ratio S/N for detection of foreign particles has usually been determined by the level of noise generated by the detection device itself, including the line sensor 9, and not by noise from the pattern 23.

According to the sixth embodiment, as described above, advantages similar to those provided by the first embodiment can be obtained. Further, the half-wave plate 31 is fitted into the detection device to detect the s-polarized laser light 17 in the detection plane 16 from the high amount of back scattered light intensity produced for the foreign particles 24. Through this arrangement, it is possible to advantageously utilize high detection S/N level, thereby enhancing the sensitivity of the detection of foreign particles.

In the detection of the sixth embodiment, through insertion of the half-wave plate 31, the s-polarized laser light 17, having a high amount of back scattered light intensity, is converted into p-polarized laser light 18 so that detection is performed by the analyzer 7, oriented to transmit only the p-polarized laser light 18. As an alternative, the analyzer of the detection device can be rotated approximately 90° to transmit only the s-polarized laser light 17.

A number of variations can be made to the sixth embodiment. For example, a photoelectric conversion element, such as a photodiode or photomultiplier, may be employed in combination with the line sensor 9 in the detection system. A slit arrangement can be used to provide a line-form illumination ray rather than the cylindrical lens 5. When used in combination with any of the second, third, fourth, and fifth embodiments, the sixth embodiment exhibits greater precision detection of the foreign particles.

Figure 19:
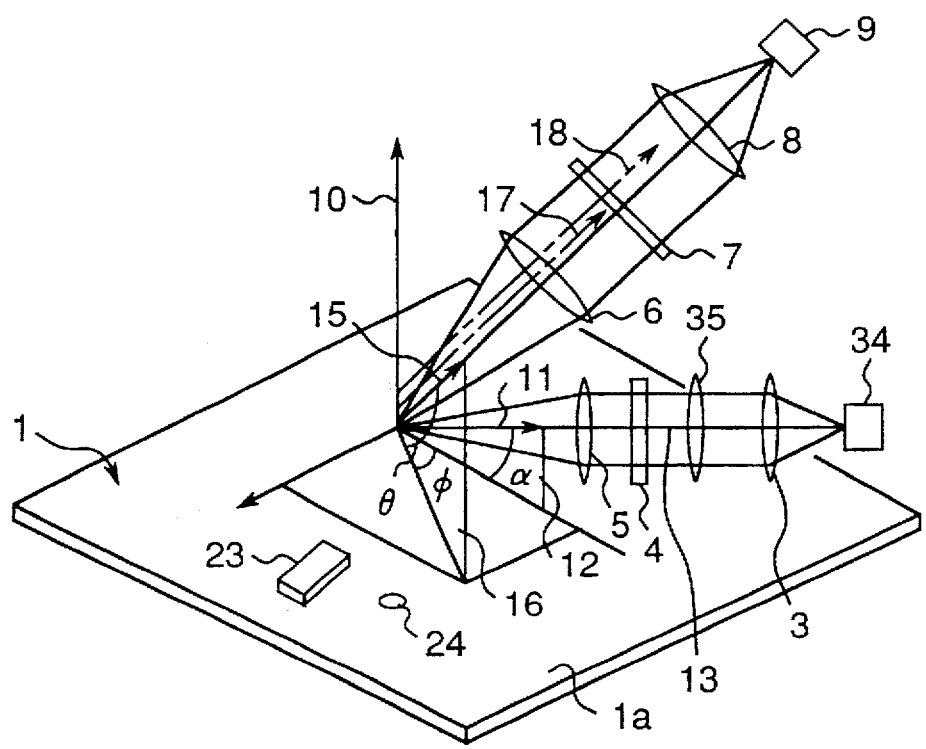
FIG. 19 is a schematic diagram showing a seventh embodiment of the invention.

FIG. 19 shows the basic configuration of the seventh embodiment of the invention. In FIG. 19, elements identical to those in FIG. 2 are designated by like numerals. The seventh embodiment differs from the first embodiment in that the illumination device includes an array-form laser light source 34 including a plurality of point sources, and a cylindrical lens 35 oriented in a direction for changing image magnification in the direction of the array.

Plural laser beams from the array-form laser light source 34 are passed through the collimator lens 3 producing parallel beams. The plural parallel laser beams are aligned into line-form parallel beams by the cylindrical lens 35. The polarizer 4, oriented to transmit the s-polarized laser beam 13 in the incident plane 12, allows the s-polarized laser beam 13 in the incident plane 12 to pass therethrough so that the cylindrical lens 5 directs the light beams so as to illuminate a line-form region on the surface of the inspection object 1 at an incident angle α which is substantially parallel to the inspection object 1.

The light thus projected for illumination is reflected by the pattern 23 on the surface of the object substrate 1. The reflected light entering the objective lens 6 is very small in light quantity due to the presence of the plane oriented in the particular direction as described in the first embodiment.

The quantity of light scattered by the foreign particles 24 is relatively larger than the quantity of light reflected from the pattern 23. Only the p-polarized laser light 18 in the detection plane 16 is allowed to pass through the analyzer 7. Correspondingly, only the p-polarized light is imaged onto the line sensor 9 by the image forming lens 8. The p-polarized laser light 18 in the detection plane 16, is photoelectrically converted by the line sensor 9 into a detection signal. Thus, high precision detection of the foreign particles 24 is possible using the detection signal of the photoelectric conversion.

The reason why the plural point sources are used will be explained. As compared with the intensity of illumination by the s-polarized laser light 13 in the incident plane 12, the intensity of the p-polarized laser light in the detection plane 16 which occurs form the foreign particles 24 is very low. Furthermore, if the foreign particles 24 are small in size, the intensity of light from the particle is much lower. This means that the detectability limits are solely dependent upon the performance of the detection device including the line sensor 9. Therefore, it is necessary to increase the quantity of illumination light by using plural light sources.

Figure 20:
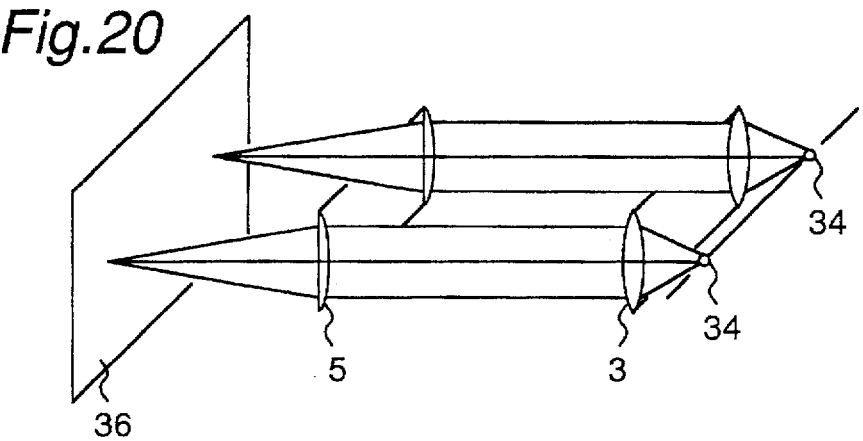
FIG. 20 is a schematic diagram showing an illumination device using an array-form light source only in the seventh embodiment.
Figure 21:
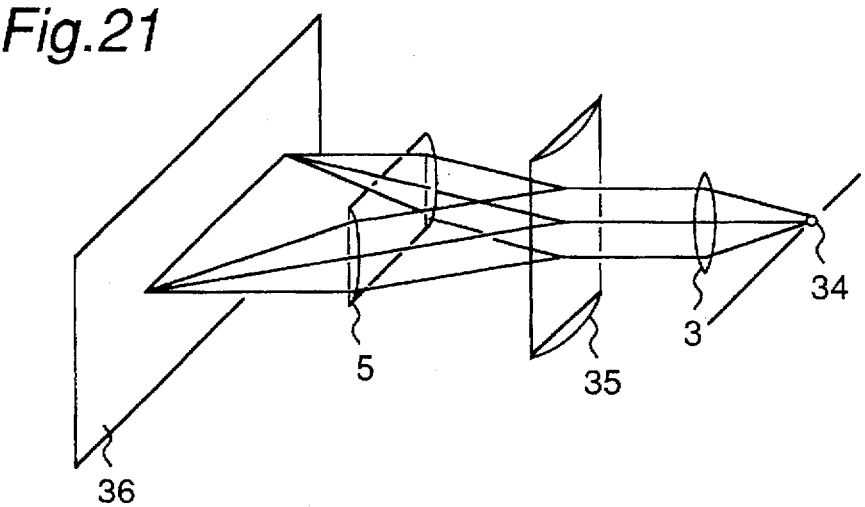
FIG. 21 is a schematic diagram showing an illumination device including an array-form light source and a cylindrical lens in the seventh embodiment.
Figure 22:
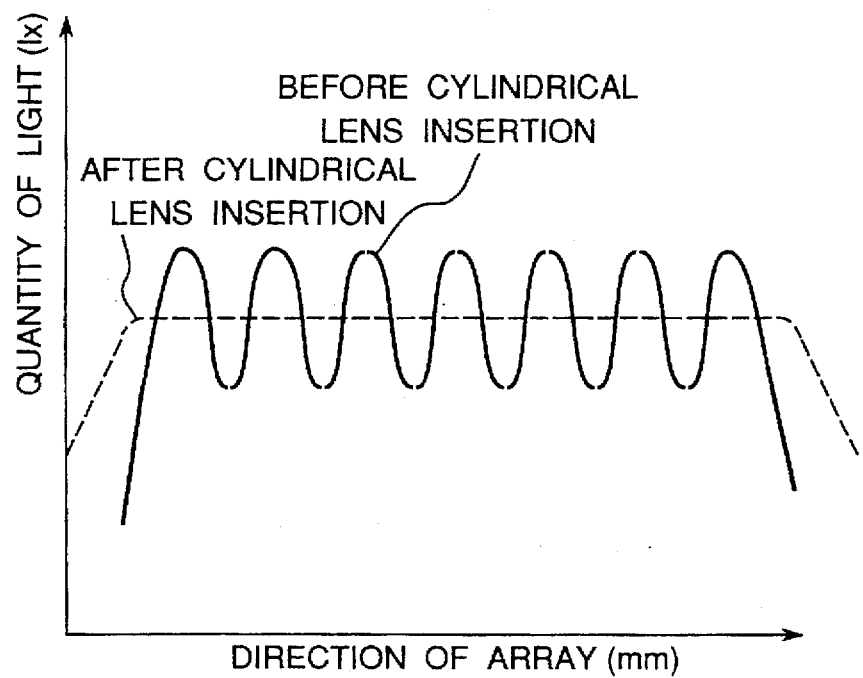
FIG. 22 is a diagram showing the intensity profile of illumination in an image forming plane in the seventh embodiment.

Next, the reasons why the cylindrical lens 35 is employed will be explained. FIG. 20 illustrates illumination from an array of a plurality of sources without the use of cylindrical lens 35. The array includes a plurality of point sources spaced at intervals. In this case, line-form illumination in the imaging plane 36 takes an intensity profile as shown by the solid lines in FIG. 22. Illumination supplied by the array of laser light sources 34 includes spaced peaks in the imaging plane 36. This poses an issue that the object may reflect in different ways depending upon the position of the field of view. It has been discovered that when a cylindrical lens 35 is disposed at an intermediate position, the rows of discrete laser beams can be suitably combined with each other. The lens must be arranged with such an orientation so as to change the image magnification in the direction of the array of laster light sources 34 as shown in FIG. 21. As a result, an intensity profile of the beams in the imaging plane 36 as shown by the dotted line in FIG. 22 can be obtained thus providing a uniform line-form illumination.

According to the seventh embodiment, as above described, advantages similar to those in the first embodiment can be obtained. Further, according to the seventh embodiment by virtue of the array-form laser light source 34 including plural point sources and the cylindrical lens 35, a uniform and more intense line-form illumination can be obtained which enables high sensitivity detection of the foreign particles 24.

A number of variations can be made to the seventh embodiment. For example a photoelectric conversion element, such as a photodiode or photomultiplier, may be employed in the detection device instead of the line sensor 9. A slit arrangement can be used to provide a line-form illumination ray rather than the cylindrical lenses 35 and 5.

Figure 23:
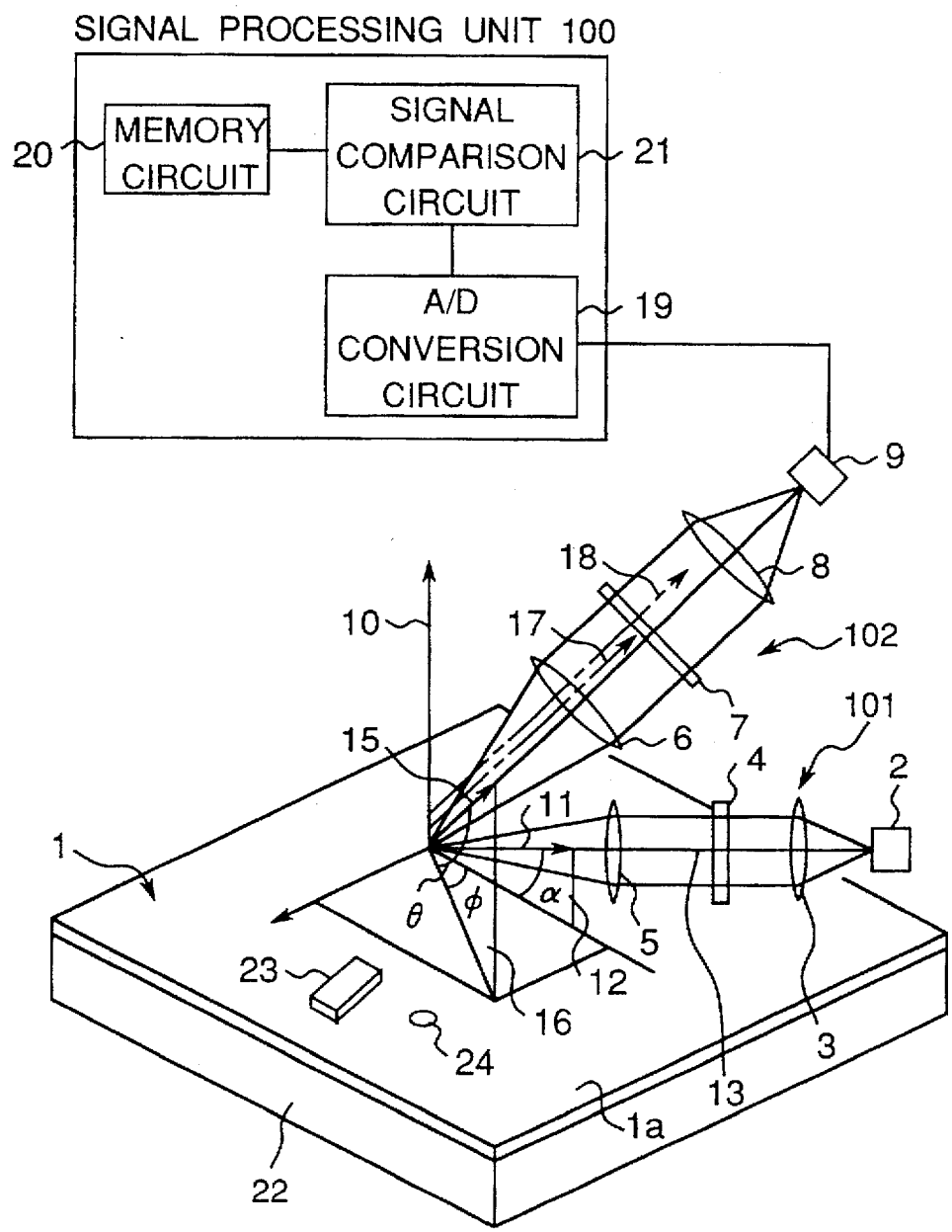
FIG. 23 is a schematic diagram showing an eighth embodiment of the invention.
Figure 24:
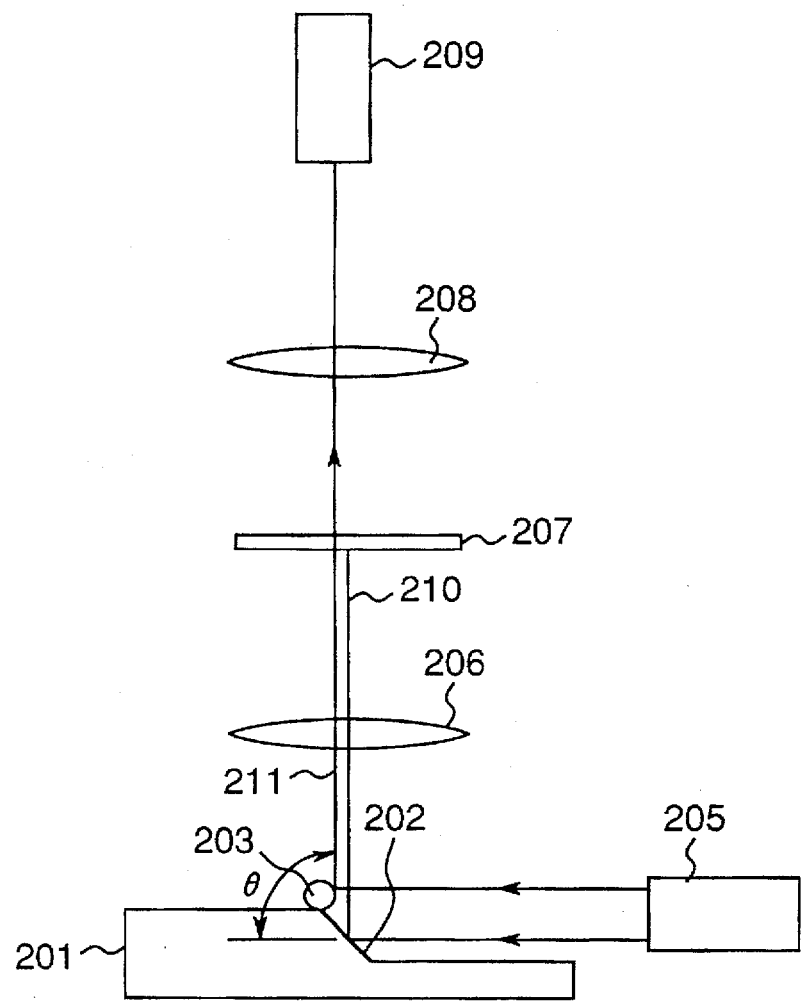
FIG. 24 is a schematic diagram showing a prior art method for foreign particles detection.
Figure 25:
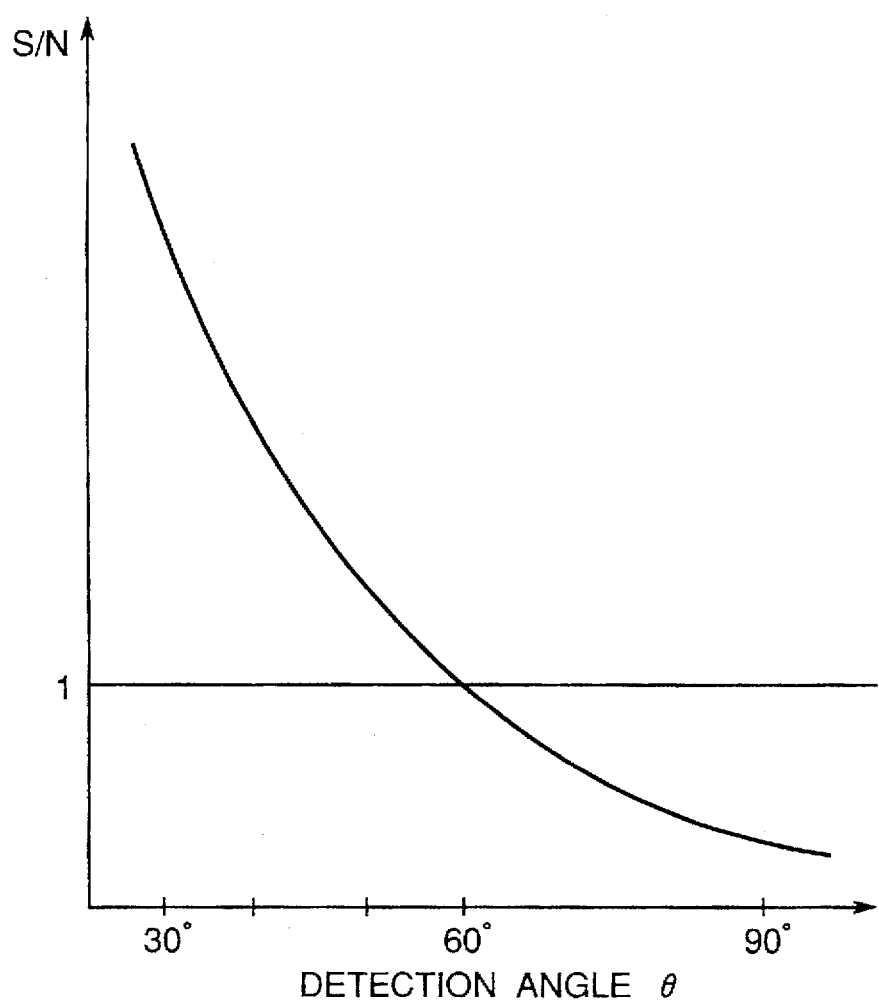
FIG. 25 is a diagram showing the relationship between detection angle and S/N in the prior art.

FIG. 23 shows the basic configuration of the eighth embodiment of the invention. In FIG. 23, elements identical to those in FIG. 2 are designated by like reference numerals.

The apparatus of the eighth embodiment is used for carrying out the method of the first embodiment. The apparatus includes an illumination device 101 having a laser light source 2, a collimator lens 3, a polarizer 4, and a cylindrical lens 5. A detection device 102 of the apparatus includes an objective lens 6, an analyzer 7, an image forming lens 8, and a line sensor 9. The apparatus also includes a signal processing unit 100 for processing a signal received from the line sensor 9 and an XY transport carriage 22 with an inspection object 1 loaded thereon. The XY transport is movable in two dimensions. The signal processing unit 100 includes an A/D conversion circuit 19 for performing A/D conversion of the output signals from the line sensor 9. The signal processing unit 100 also includes a memory circuit 20 having stored therein threshold values preset for the detection of the foreign particles 24. The signal processing unit 100 further includes a signal comparison circuit 21 for comparing an output from an A/D conversion circuit 19 with the threshold value stored in the memory circuit 20.

In operation, laser beams from the laser light source 2 are passed through the collimator lens 3 producing parallel beams. The s-polarized laser light 13 in the incident plane 12 is allowed to pass through the polarizer 4. The azimuth of the polarizer is adapted to transmit the s-polarized laser light 13. A line-form area on the surface of the object substrate 1 is illuminated through the cylindrical lens 5 at an incident angle α which is generally parallel to the object substrate 1.

Light rays supplied in this way are reflected from the pattern 23 on the surface of the inspection object 1. The quantity of light entering the objective lens 6 from the pattern 23 is very small. The quantity of light scattered by the foreign particles 24 is relatively larger than that of the light reflected from the pattern 23. For portions of the reflected light from the pattern 23 and the scattered light from the foreign particles 24 which enter the objective lens 6, only the p-polarized laser light 18 in the detection plane 16 is allowed to pass through the analyzer 7. The p-polarized light is then imaged onto the line sensor 9 by the image forming lens 8. The p-polarized laser light 18 in the detection plane 16, as already described with respect to the first embodiment, is photoelectrically converted by the line sensor 9 into a detection signal.

In the eighth embodiment, each detection signal is subjected to A/D conversion by the A/D conversion circuit 19. An output signal from the A/D conversion circuit is compared, in the comparison circuit, with the threshold value preset in the memory circuit 20. Subsequently, the XY transport carriage 22 is moved for sequential inspection of the foreign particles 24 over the entire surface of the object substrate 1.

A number of variations can be made to the eighth embodiment. For example, a photoelectric conversion element, such as photodiode or photomultiplier, may be used as the detection device instead of the line sensor 9. The sample transport means may be capable of rotary movement and shift movement in combination. A slit arrangement or the like can be used to provide a line-form illumination ray rather than the cylindrical lens 5. The eighth embodiment may be employed in combination with any of the second through seventh embodiments in order to provide higher precision inspection of foreign particles 24.

Many modifications and variations of the present invention are possible in light of the above teachings and within the scope of the appended claims.

According to the present invention, the intensity of detection light from the foreign particles can be improved with respect to the intensity of detection light reflected from the pattern or the like. The present invention thus enables detection of even very minute foreign particles.

By arranging the angle between the optical axis of the beam and the inspection surface of the object within the range of 1°≦x<5°, it is possible to further improve the distinction between the foreign particles and the pattern, and to thus achieve detection of foreign particles with greater precision. Furthermore, by carrying out the detection of foreign particles with an optical axis that makes an angle of less than 60° with the inspection surface, it is possible to further improve the distinction between the foreign particles and the pattern, and to thus achieve detection with greater precision.

When the detection of the foreign particles is carried out with an optical axis that makes an angle of 40° or less with the inspection surface of the inspection object, the distinction between the foreign particles and the pattern can be improved even outside the optical axis, thus making it possible to achieve such detection with greater precision.

The provision of a spatial filter, for removal of a periodic pattern at a detection device, permits elimination of light rays from the pattern of the inspection object. This makes it possible to achieve higher precision detection of the foreign particles.

The provision at the detection device of an optical system designed to have a larger aperture outside the optical axis than a confocal optical system enables reception of a larger quantity of light from the foreign particles outside the optical axis. This makes it possible to achieve higher precision detection of the foreign particles outside the optical axis.

The provision of a telecentric optical system in the detection device makes it possible to achieve proper magnification without impairment of the magnification when the inspection object is subject to some undulation. This provides for high precision detection of the foreign particles.

The provision in the detection device of a half-wave plate, and a wave plate movement control device adapted for insertion and removal of the half-wave plate according to the type of the inspection object, permits the selection of a direction of polarization in which greater intensity of light is obtainable. This provides for high sensitivity detection of the foreign particles.

The provision in the illumination device of a plurality of point sources, and of a cylindrical lens disposed so as to vary the magnification of an image oriented in a direction parallel with the array of beams, enables supply of a line beam with higher and more uniform intensity. This provides for high precision detection of the foreign particles.

The foreign particles inspecting apparatus of the invention, constructed as above described, is unlikely to receive light rays from components such as the pattern of the object. These components may be a cause of noise generation. With the apparatus, therefore, it is possible to achieve high precision inspection of the foreign particles.

Although the present invention has already been fully described in connection with the preferred embodiments thereof with reference to the accompanying drawings,it is to be noted that various changes and modifications are apparent to those skilled in the art. Such changes and modifications are to be understood as included within the scope of the present invention as defined by the appended claims unless they depart therefrom.

What is claimed is:

1. A method of foreign particles inspection comprising:
    illuminating an inspection surface of an inspected object with a beam, which is one of an s-polarized light and a p-polarized light relative to the inspection surface of the inspection object, in such a manner that an optical axis of the beam intersects the inspection surface at an angle of not less than 1° and less than 5°; and
    detecting, as an indication of foreign particles, a component of reflected and scattered light which occurs from the beam and which is the other of the s-polarized light and the p-polarized light, wherein said detecting is about a detection optical axis which makes an acute angle with the inspection surface and which makes a differential angle of 30° or less with the optical axis of the beam.

2. The method of foreign particles inspection as claimed in claim 1, wherein:
    the inspection object is a patterned substrate; and
    the detecting comprises comparing:
        a light quantity of a polarized light component of the reflected light, which indicates the presence of foreign particles with
        a light quantity of a polarized light component of the scattered light.

3. The method of foreign particles inspection as claimed in claim 1, wherein said detecting is about a detection optical axis which makes an angle of less than 60° with the inspection surface of the inspection object.

4. The method of foreign particles inspection as claimed in claim 2, wherein said detecting is about a detection optical axis which makes an angle of less than 60° with the inspection surface of the inspection object.

5. The method of foreign particles inspection as claimed in claim 3, wherein said detecting is about a detection optical axis which makes an angle of 40° or less with the inspection surface of the inspection object.

6. The method of foreign particles inspection as claimed in claim 4, wherein said detecting is about a detection optical axis which makes an angle of 40° or less with the inspection surface of the inspection object.

7. The method of foreign particles inspection as claimed in claim 1, wherein a periodic pattern of the inspection object is eliminated by disposing a spatial filter along the detection optical axis.

8. The method of foreign particles inspection as claimed in claim 2, wherein a periodic pattern of the inspection object is eliminated by disposing a spatial filter along the detection optical axis.

9. The method of foreign particles inspection as claimed in claim 5, wherein a periodic pattern of the inspection object is eliminated by disposing a spatial filter along the detection optical axis.

10. The method of foreign particles inspection as claimed in claim 1, wherein , as an indication of the foreign particles, a p-polarized component of the reflected and scattered light is detected about the detection optical axis and by using an optical system, and a photoelectric conversion element, wherein the optical system comprises an objective lens having a focal length f and an aperture diameter D, and an image forming lens having a principal plane located at a distance L from a principal plane of the objective lens, the image forming lens having an aperture diameter set to be (D−2A+AL/f) or more, where A denotes an inspection width determined based on a magnification relationship between detection ranges of the photoelectric conversion element and the objective and image forming lenses.

11. The method of foreign particles inspection as claimed in claim 2, wherein a, as an indication of the foreign particles, a p-polarized component of the reflected and scattered light is detected about the detection optical axis and by using an optical system, and a photoelectric conversion element, wherein the optical system comprises an objective lens having a focal length f and an aperture diameter D, and an image forming lens having a principal plane located at a distance L from a principal plane of the objective lens, the image forming lens having an aperture diameter set to be (D−2A+AL/f) or more, where A denotes an inspection width determined based on a magnification relationship between detection ranges of the photoelectric conversion element and the objective and image forming lenses.

12. The method of foreign particles inspection as claimed in claim 1, wherein a p-polarized component of the reflected and scattered light is detected, as an indication of the foreign particles, by using a telecentric optical system.

13. The method of foreign particles inspection as claimed in claim 2, wherein a p-polarized component in the reflected and scattered light is detected, as an indication of the foreign particles, by using a telecentric optical system.

14. The method of foreign particles inspection as claimed in claim 1, wherein a half-wave plate for rotating polarized light is added so that an s-polarized component in the reflected and scattered light is converted into a p-polarized component, the p-polarized component is detected as an indication of the foreign particles, about the detection optical axis.

15. The method of foreign particles inspection as claimed in claim 2, wherein a half-wave plate for rotating polarized light is added so that an s-polarized component in the reflected and scattered light is converted into a p-polarized component, the p-polarized light component is detected, as an indication of the foreign particles, about the detection optical axis.

16. The method of foreign particles inspection as claimed in claim 1, wherein beams from an array of point sources are set as a line beam by a cylindrical lens disposed so as to vary a magnification of an image oriented in a direction parallel with the array of point sources.

17. The method of foreign particles inspection as claimed in claim 2, wherein beams from an array of point sources are set as a line beam by a cylindrical lens disposed so as to vary a magnification of an image oriented in a direction parallel with the array of point sources.

18. A foreign particles inspecting apparatus comprising:
an illumination device arranged so as to define an optical axis substantially parallel to an inspection surface of an inspection object, for supplying a beam of light toward the inspection surface of the inspection object wherein the beam is one of s-polarized and ppolarized relative to the inspection surface;
a detection device having a detection optical axis which makes an acute angle with the inspection surface of the inspection object and which makes a differential angle of 30° or less with the optical axis of the illumination device, such that said detection device can detect a light component in reflected and scattered light produced by the illumination device, which is the other of s-polarized and p-polarized relative to the inspection surface, and performs photoelectric conversion of the light component; and
a signal processing unit for determining foreign particles based on a signal from the photoelectric conversion from the detection device.

19. The foreign particles inspecting apparatus as claimed in claim 18, wherein:
the inspection object is a patterned substrate; and
the detection device is capable of comparing:

a light quantity of a polarized light component of the reflected light, which indicates the presence of foreign particles with
a light quantity of a polarized light component of the scattered light.

20. The foreign particles inspecting apparatus as claimed in claim 18, wherein said detecting device has a detection optical axis which makes an angle of less than 60° with the inspection surface of the inspection object.

21. The foreign particles inspecting apparatus as claimed in claim 19, wherein said detecting device has a detection optical axis which makes an angle of less than 60° with the inspection surface of the inspection object.

22. The foreign particles inspecting apparatus as claimed in claim 20, wherein said detecting device has a detection optical axis which makes an angle of 40° or less with the inspection surface of the inspection object.

23. The foreign particles inspecting apparatus as claimed in claim 21, wherein said detecting device has a detection optical axis which makes an angle of 40< or less with the inspection surface of the inspection object.

24. The foreign particles inspecting apparatus as claimed in claim 18 further comprising a spatial filter disposed along the detection optical axis.

25. The foreign particles inspecting apparatus as claimed in claim 19 further comprising a spatial filter disposed along the detection optical axis.

26. The foreign particles inspecting apparatus as claimed in claim 22 further comprising a spatial filter disposed along the detection optical axis.

27. The foreign particles inspecting apparatus as claimed in claim 18 further comprising an optical system, and a photoelectric conversion element, wherein the optical system comprises an objective lens having a focal length f and an aperture diameter D, and an image forming lens having a principal plane located at a distance L from a principal plane of the objective lens, the image forming lens having an aperture diameter set to be (D−2A+AL/f) or more, where A denotes an inspection width determined based on a magnification relationship between detection ranges of the photoelectric conversion element and the objective and image forming lenses.

28. The foreign particles inspecting apparatus as claimed in claim 19 further comprising an optical system, and a photoelectric conversion element, wherein the optical system comprises an objective lens having a focal length f and an aperture diameter D, and an image forming lens having a principal plane located at a distance L from a principal plane of the objective lens, the image forming lens having an aperture diameter set to be (D−2A+AL/f) or more, where A denotes an inspection width determined based on a magnification relationship between detection ranges of the photoelectric conversion element and the objective and image forming lenses.

29. The foreign particles inspecting apparatus as claimed in claim 18 further comprising a telecentric optical system for use in detecting a p-polarized component of the reflected and scattered light.

30. The foreign particles inspecting apparatus as claimed in claim 19 further comprising a telecentric optical system for use in detecting a p-polarized component of the reflected and scattered light.

31. The foreign particles inspecting apparatus as claimed in claim 18 further comprising a half-wave plate for rotating polarized light so that an s-polarized component in the reflected and scattered light is converted into a p-polarized component.

32. The foreign particles inspecting apparatus as claimed in claim 19 further comprising a half-wave plate for rotating polarized light so that an s-polarized component in the reflected and scattered light is converted into a p-polarized component.

33. The foreign particles inspecting apparatus as claimed in claim 18 further comprising an array of point sources and a cylindrical lens, wherein beams from the array of point sources are set as a line beam by the cylindrical lens disposed so as to vary a magnification of an image oriented in a direction parallel with the array of point sources.

34. The foreign particles inspecting apparatus as claimed in claim 19 further comprising an array of point sources and a cylindrical lens, wherein beams from the array of point sources are set as a line beam by the cylindrical lens disposed so as to vary a magnification of an image oriented in a direction parallel with the array of point sources.

35. A method of foreign particles inspection comprising:

producing parallel beams by passing laser beams from a laser light source through a collimator lens;

passing only one of s-polarized light and p-polarized light from the parallel beams through a polarizer;

directing the light passed by the polarizer through a cylindrical lens so as to illuminate a line-form region on an inspection surface of an inspection object, on an incident plane, at an incident angle that is greater than or equal to 1° and less than 5° with respect to the inspection object;

wherein the light on the incident plane is reflected by a pattern on the inspection surface of the inspection object or is scattered by foreign particles on the inspection surface of the inspection object;

receiving, about a detection optical axis which makes an acute angle with the inspection surface, the reflected and scattered light by an objective lens;

transmitting, through an analyzer, only the other of s-polarized light and p-polarized light from the light received by the objective lens;

focusing the light from the analyzer by an image forming lens onto a line sensor;

photoelectrically converting the focused light into a detection signal by the line sensor; and detecting the foreign particles based on the detection signal.

36. The method of foreign particles inspection as claimed in claim 35, wherein receiving is about a detection optical axis which makes an angle of less than 60° with the inspection surface of the inspection object, and which makes a differential of 0° with the light from the cylindrical lens.

* * * * *